United States Patent
Yoshida et al.

(10) Patent No.: US 10,650,267 B2
(45) Date of Patent: May 12, 2020

(54) MEDICAL IMAGE PROCESSING APPARATUS

(71) Applicant: Toshiba Medical Systems Corporation, Otawara-shi (JP)

(72) Inventors: Masashi Yoshida, Nasushiobara (JP); Kousuke Sakaue, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 74 days.

(21) Appl. No.: 15/001,972

(22) Filed: Jan. 20, 2016

(65) Prior Publication Data
US 2016/0210745 A1 Jul. 21, 2016

(30) Foreign Application Priority Data

Jan. 20, 2015 (JP) ................................. 2015-008776
Jan. 18, 2016 (JP) ................................. 2016-007143

(51) Int. Cl.
G06K 9/00 (2006.01)
G06K 9/62 (2006.01)
G06F 19/00 (2018.01)

(52) U.S. Cl.
CPC ......... G06K 9/6201 (2013.01); G06F 19/321 (2013.01)

(58) Field of Classification Search
CPC ........ G06F 19/30; G06F 19/32; G06F 19/321; G06F 19/322; G06F 19/324; G06F 19/327
See application file for complete search history.

(56) References Cited

U.S. PATENT DOCUMENTS

| | | | | |
|---|---|---|---|---|
| 6,954,767 B1* | 10/2005 | Kanada | ................ | G06F 16/51 |
| 7,016,952 B2* | 3/2006 | Mullen | ............... | G06F 11/0709 |
| | | | | 705/2 |
| 7,187,790 B2* | 3/2007 | Sabol | ..................... | G06Q 10/10 |
| | | | | 382/128 |
| 7,523,505 B2* | 4/2009 | Menschik | .............. | G16H 10/60 |
| | | | | 726/26 |
| 8,019,626 B2* | 9/2011 | Mahesh | ................. | G06Q 10/00 |
| | | | | 705/3 |

(Continued)

FOREIGN PATENT DOCUMENTS

| | | |
|---|---|---|
| JP | 2003-248723 A | 9/2003 |
| JP | 2003-323493 | 11/2003 |

(Continued)

OTHER PUBLICATIONS

Office Action dated Jul. 23, 2019 in Japanese Patent Application No. 2016-007143.

(Continued)

*Primary Examiner* — Avinash Yentrapati
(74) *Attorney, Agent, or Firm* — Oblon, McClelland, Maier & Neustadt, L.L.P.

(57) ABSTRACT

According to one embodiment, a medical image processing apparatus includes a memory, an information collector and a determiner. The memory stores DICOM image data including study information. The information collector collects information relating to general-purpose image data incompatible with DICOM. The determiner determines whether designated general-purpose image data is related to a study which generates the DICOM image data, based on information collected by the information collector and the study information.

15 Claims, 21 Drawing Sheets

(56) References Cited

U.S. PATENT DOCUMENTS

| | | | | |
|---|---|---|---|---|
| 8,560,968 B1* | 10/2013 | Nair | | G16H 40/63 |
| | | | | 715/839 |
| 9,104,985 B2* | 8/2015 | Drucker | | G06Q 10/00 |
| 2003/0140141 A1* | 7/2003 | Mullen | | G06F 11/0709 |
| | | | | 709/225 |
| 2003/0208378 A1* | 11/2003 | Thangaraj | | G06F 19/321 |
| | | | | 705/2 |
| 2004/0034550 A1* | 2/2004 | Menschik | | G16H 10/60 |
| | | | | 705/3 |
| 2004/0120557 A1* | 6/2004 | Sabol | | G06Q 10/10 |
| | | | | 382/128 |
| 2004/0141661 A1* | 7/2004 | Hanna | | G06F 19/321 |
| | | | | 382/305 |
| 2004/0249677 A1* | 12/2004 | Datta | | G06Q 50/24 |
| | | | | 705/3 |
| 2004/0249806 A1* | 12/2004 | Kanada | | G06F 16/51 |
| 2005/0027995 A1* | 2/2005 | Menschik | | G06F 19/321 |
| | | | | 713/193 |
| 2005/0158767 A1* | 7/2005 | Haskell | | G06Q 50/24 |
| | | | | 435/6.11 |
| 2005/0182657 A1* | 8/2005 | Abraham-Fuchs | | G06Q 50/22 |
| | | | | 705/2 |
| 2005/0207658 A1* | 9/2005 | Schofield | | G06F 19/321 |
| | | | | 382/232 |
| 2005/0246629 A1* | 11/2005 | Hu | | G06F 17/2247 |
| | | | | 715/237 |
| 2006/0155585 A1* | 7/2006 | Onishi | | G06F 19/321 |
| | | | | 705/3 |
| 2006/0229911 A1* | 10/2006 | Gropper | | G06F 19/321 |
| | | | | 705/2 |
| 2006/0239573 A1* | 10/2006 | Novatzky | | G01S 7/52098 |
| | | | | 382/239 |
| 2006/0242144 A1* | 10/2006 | Esham | | G06F 19/321 |
| 2006/0242159 A1* | 10/2006 | Bishop | | G06F 19/321 |
| 2007/0118540 A1* | 5/2007 | Guo | | G06F 16/58 |
| 2007/0292012 A1* | 12/2007 | Brandon | | G06F 19/321 |
| | | | | 382/128 |
| 2008/0052112 A1* | 2/2008 | Zahlmann | | G06F 19/321 |
| | | | | 705/2 |
| 2008/0085045 A1* | 4/2008 | Tago | | G06F 19/321 |
| | | | | 382/132 |
| 2010/0042653 A1* | 2/2010 | Krishnan | | G16H 30/20 |
| | | | | 715/205 |
| 2010/0211409 A1* | 8/2010 | Kotula | | G06Q 10/06 |
| | | | | 705/3 |
| 2011/0110568 A1* | 5/2011 | Vesper | | G06F 19/321 |
| | | | | 382/128 |
| 2011/0129129 A1* | 6/2011 | Avinash | | A61B 5/04 |
| | | | | 382/128 |
| 2011/0176712 A1* | 7/2011 | Hill | | G06F 19/321 |
| | | | | 382/128 |
| 2011/0188718 A1* | 8/2011 | Hill | | G16H 30/20 |
| | | | | 382/128 |
| 2011/0295873 A1* | 12/2011 | Potter | | G06F 19/321 |
| | | | | 707/769 |
| 2012/0243754 A1* | 9/2012 | Koff | | G06F 19/321 |
| | | | | 382/128 |
| 2014/0149407 A1* | 5/2014 | Qian | | G06F 19/321 |
| | | | | 707/737 |
| 2016/0092748 A1* | 3/2016 | Koktava | | G06K 9/6201 |
| | | | | 382/128 |
| 2016/0350480 A1* | 12/2016 | Gerdeman | | G06F 19/321 |

FOREIGN PATENT DOCUMENTS

| | | |
|---|---|---|
| JP | 2004-97651 | 4/2004 |
| JP | 2004-154560 A | 6/2004 |
| JP | 2004-290259 | 10/2004 |
| JP | 2005-149111 | 6/2005 |
| JP | 2006-271810 | 10/2006 |
| JP | 2013-77321 A | 4/2013 |
| JP | 2013-250903 A | 12/2013 |
| JP | 2014-209340 A | 11/2014 |
| WO | WO 2013/111033 A2 | 8/2013 |

OTHER PUBLICATIONS

Japanese Office Action dated Mar. 3, 2020, issued in Japanese Patent Application No. 2016-007143.

* cited by examiner

401  Study information list

| Study ID | Kind of study | Patient ID | Patient name | Date of study | Operator name | |
|---|---|---|---|---|---|---|
| --- | --- | --- | --- | --- | --- | --- |
| 10077 | X-ray examination | 168 | Joe Smith | 2014/01/10 | T T | --- |
| 0123456 | CT examination | 168 | Joe Smith | 2014/01/10 | T T | --- |
| 2266 | MRI examination | 401 | Taro Yamada | 2014/01/25 | S. A | --- |
| 4488 | Living tissue diagnosis | 168 | Joe Smith | 2014/02/25 | B. C | --- |
| 7555 | Surgical operation | 168 | Joe Smith | 2014/03/14 | Y. M | --- |
| 1568 | Pathological diagnosis of tissue | 168 | Joe Smith | 2014/03/15 | T M | --- |
| 7556 | Surgical operation | 401 | Taro Yamada | 2014/03/16 | A. D | --- |
| --- | --- | --- | --- | --- | --- | --- |

401 File information

| Folder/file | Camera image, Joe Smith/IMG010 |
|---|---|
| Date | 2014/01/08 14:16:25 |
| Operator ID | p9876543 |
| Meta data | Pathological examination |

F I G. 5A

71 Comparison information

| Patient name | Joe Smith |
|---|---|
| Date of study | 2014/01/08 |
| Operator name | T. M |
| Kind of study | Pathological diagnosis of tissue |

F I G. 5B

81 List

| Study ID | Kind of study | Patient ID | Patient name | Date of study | Operator name | |
|---|---|---|---|---|---|---|
| 10077 | X-ray examination | 168 | Joe Smith | 2014/01/10 | T. T | ------- |
| 0123456 | CT examination | 168 | Joe Smith | 2014/01/10 | T. T | ------- |
| 4488 | Living tissue diagnosis | 168 | Joe Smith | 2014/02/25 | B. C | ------- |
| 7555 | Surgical operation | 168 | Joe Smith | 2014/03/14 | Y. M | ------- |
| 1568 | Pathological diagnosis of tissue | 168 | Joe Smith | 2014/03/15 | T. M | ------- |

F I G. 6

23 Window

⚠ WARNING

The image to be pasted may be that of an unrelated patient

Study supposed from image

| Kind of study | Pathological diagnosis of tissue |
|---|---|
| Date of study | 2014/01/08 |

List of patients related to pasting

| Study ID | Kind of study | Patient ID | Patient name | Date of study | Operator name | |
|---|---|---|---|---|---|---|
| 10077 | X-ray examination | 168 | Joe Smith | 2014/01/10 | T T | ------ |
| 0123456 | CT examination | 168 | Joe Smith | 2014/01/10 | T T | ------ |
| 4488 | Living tissue diagnosis | 168 | Joe Smith | 2014/02/25 | B. C | ------ |
| 7555 | Surgical operation | 168 | Joe Smith | 2014/03/14 | Y. M | ------ |
| 1568 | Pathological diagnosis of tissue | 168 | Joe Smith | 2014/03/15 | T M | ------ |

F I G. 7

401a  File information

| Folder/file | Camera image, Joe Smith/IMG010 |
|---|---|
| Date | 2014/01/08 14:16:25 |
| Operator ID | p9876543 |

F I G. 8A

71a  Comparison information

| Patient name | Joe Smith |
|---|---|
| Date of study | 2014/01/08 |
| Operator name | T. M |

F I G. 8B

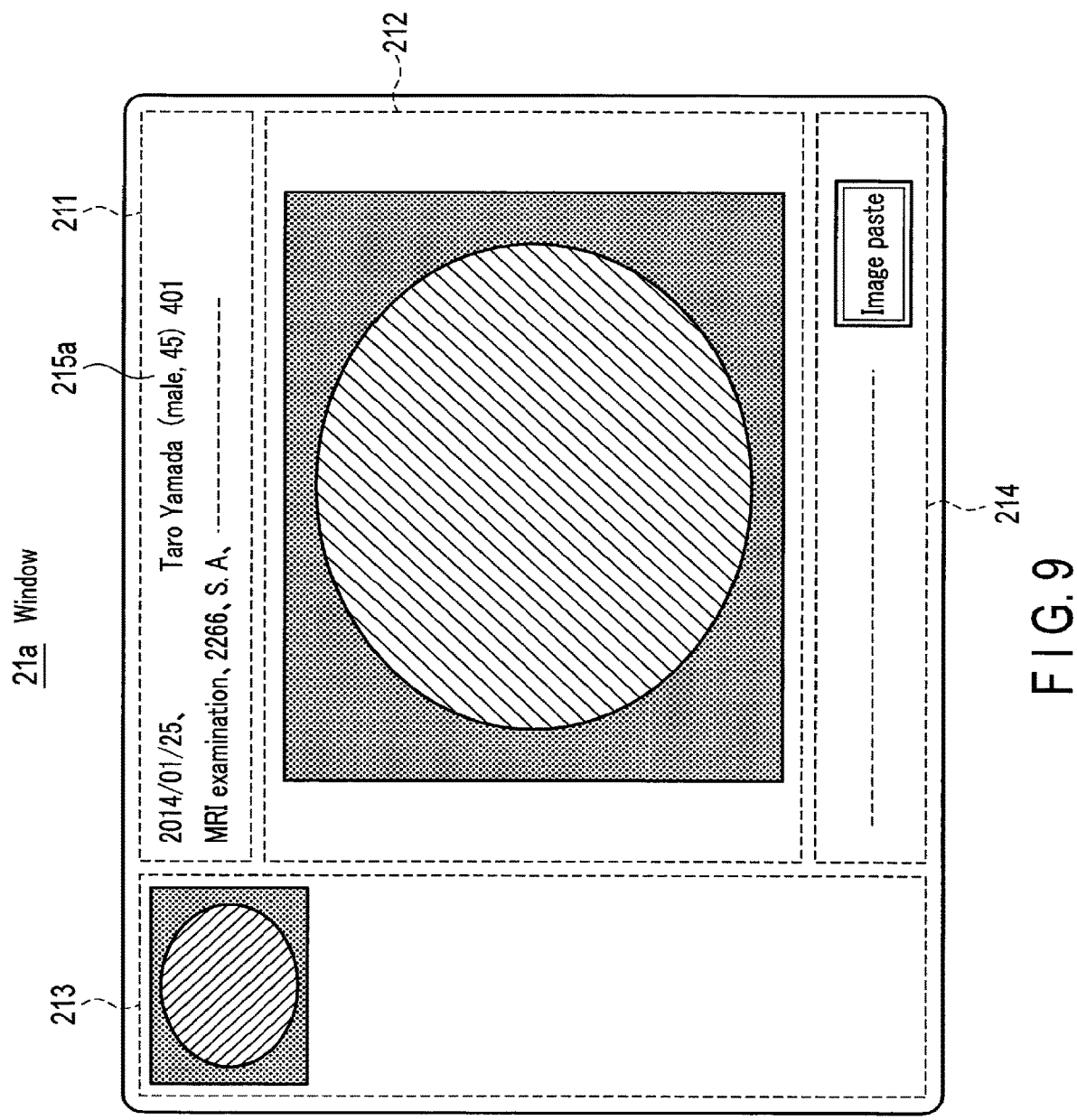
F I G. 9

FIG. 10

51　General-purpose image data
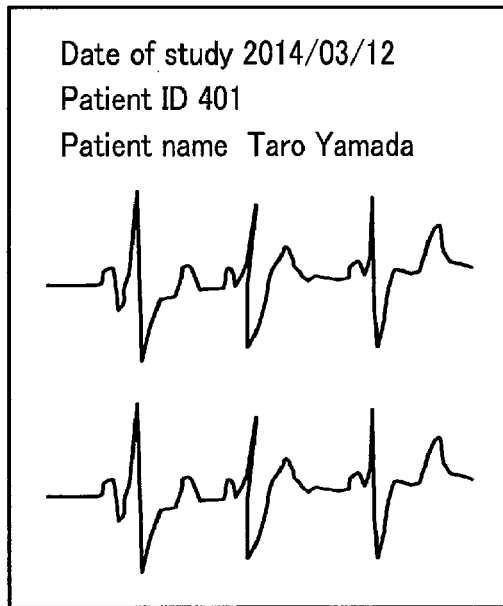
F I G. 11
401b　File information
| Folder/file | Scan image/ · · · · · |
|---|---|
| Date of study | 2014/03/12 |
| Patient ID | 401 |
| Patient name | Taro Yamada |
| Meta data | Electrocardiogram |
F I G. 12A 71b   Comparison information

| Date of study | 2014/03/12 |
|---|---|
| Patient ID | 401 |
| Patient name | Taro Yamada |
| Kind of study | Electrocardiogram |

F I G. 12B

401c  File information

| Folder/file | Scan image/··· |
|---|---|
| Date | 2014/03/09 14:11:52 |
| Model | TC copy/scanner |
| Product serial number | 9998876 |

F I G. 14A

71c  Comparison information

| Date of study | 2014/03/09 |
|---|---|
| Kind of study | Electrocardiogram |

F I G. 14B

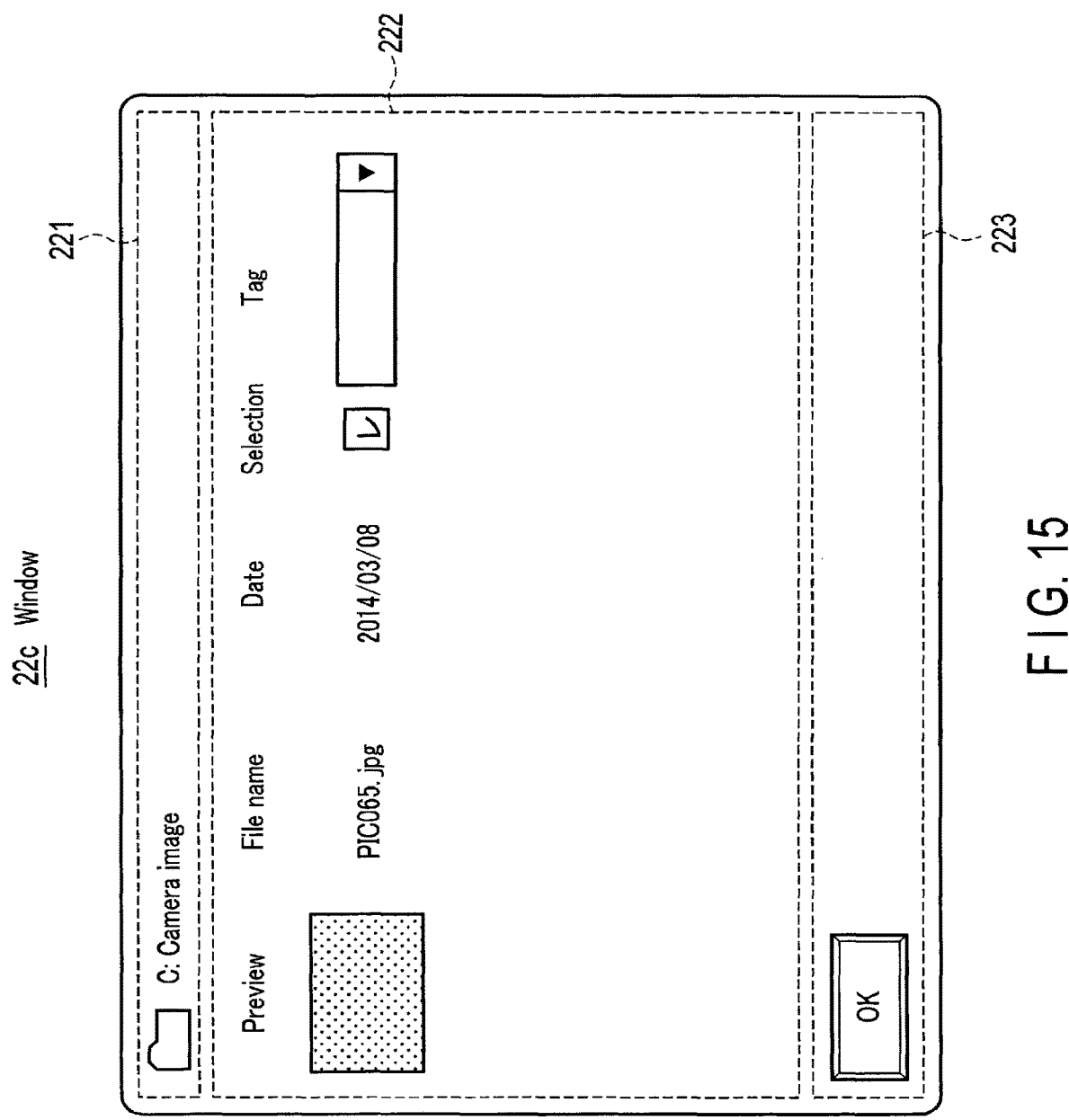
F I G. 15

401d  File information

| Folder/file | Camera image/PIC065 |
|---|---|
| Date | 2014/03/08 15:12:34 |
| Location information | Operating room |

F I G. 16A

71d  Comparison information

| Date of study | 2014/03/08 |
|---|---|
| Kind of study | Surgical operation, ultrasonic diagnosis during operation |

F I G. 16B

MEDICAL IMAGE PROCESSING APPARATUS

CROSS-REFERENCE TO RELATED APPLICATIONS

This application is based upon and claims the benefit of priority from Japanese Patent Applications No. 2015-008776, filed Jan. 20, 2015, and No. 2016-007143, filed Jan. 18, 2016, the entire contents of which are incorporated herein by reference.

FIELD

Embodiments described herein relate generally to a medical image processing apparatus.

BACKGROUND

Medical image diagnosis apparatuses, such as an X-ray diagnosis apparatus, an X-ray computed tomography (CT) apparatus, an MRI apparatus, an ultrasonic diagnosis apparatus and a nuclear medical diagnosis apparatus, are known in the art. Medical image data obtained when subjects are examined by these apparatuses are stored in medical image memories, using the format based on the Digital Imaging and COmmunication in Medicine (DICOM). A file compatible with the DICOM includes medical image data and study information attached to the medical image data. The study information includes a study ID for identifying a study, a modality ID for identifying a modality used for capturing medical image data during the study, and a patient ID for identifying a subject.

An image managing system capable of recording image data such as a digital camera image (hereinafter referred to as general-purpose image data) in a medical image storage apparatus in association with medical image data is also known in the art. With the existing technology, however, incorrect association of images may occur, which associates irrelevant general-purpose image data with medical image data. The general-purpose data is JPEG (joint photographic experts group) data, and this kind of data does not include information that identifies an individual patient or individual study.

BRIEF DESCRIPTION OF THE DRAWINGS

FIG. 2 shows an example of a list of study information stored in a study information storage apparatus;

FIG. 4 shows an example of a user interface used for designating general-purpose image data;

FIG. 5A shows an example of file information;

FIG. 5B shows an example of comparison information prepared based on the file information depicted in FIG. 5A.

FIG. 6 shows an example of a study list;

FIG. 7 shows an example of a window in which a warning message is displayed;

FIG. 8A shows another example of file information;

FIG. 8B shows an example of comparison information prepared based on the file information depicted in FIG. 8A;

FIG. 9 shows another example of a window used for displaying a medical image;

FIG. 10 shows another example of a user interface used for designating general-purpose image data;

FIG. 11 shows an example of general-purpose image data captured by an image scanner;

FIG. 12A shows another example of file information;

FIG. 12B shows an example of comparison information prepared based on the file information depicted in FIG. 12A;

FIG. 14A shows another example of file information;

FIG. 14B shows an example of comparison information prepared based on the file information depicted in FIG. 14A.

FIG. 15 shows another example of a user interface used for designating general-purpose image data;

FIG. 16A shows another example of file information;

FIG. 16B shows an example of comparison information prepared based on the file information depicted in FIG. 16A.

DETAILED DESCRIPTION

In general, according to one embodiment, a medical image processing apparatus includes a memory, an information collector and a determiner. The memory stores DICOM (Digital Imaging and COmmunication in Medicine) image data including study information. The information collector collects information relating to general-purpose image data incompatible with DICOM. The determiner determines whether designated general-purpose image data is related to a study which generates the DICOM image data, based on information collected by the information collector and the study information.

First Embodiment

Figure 1:
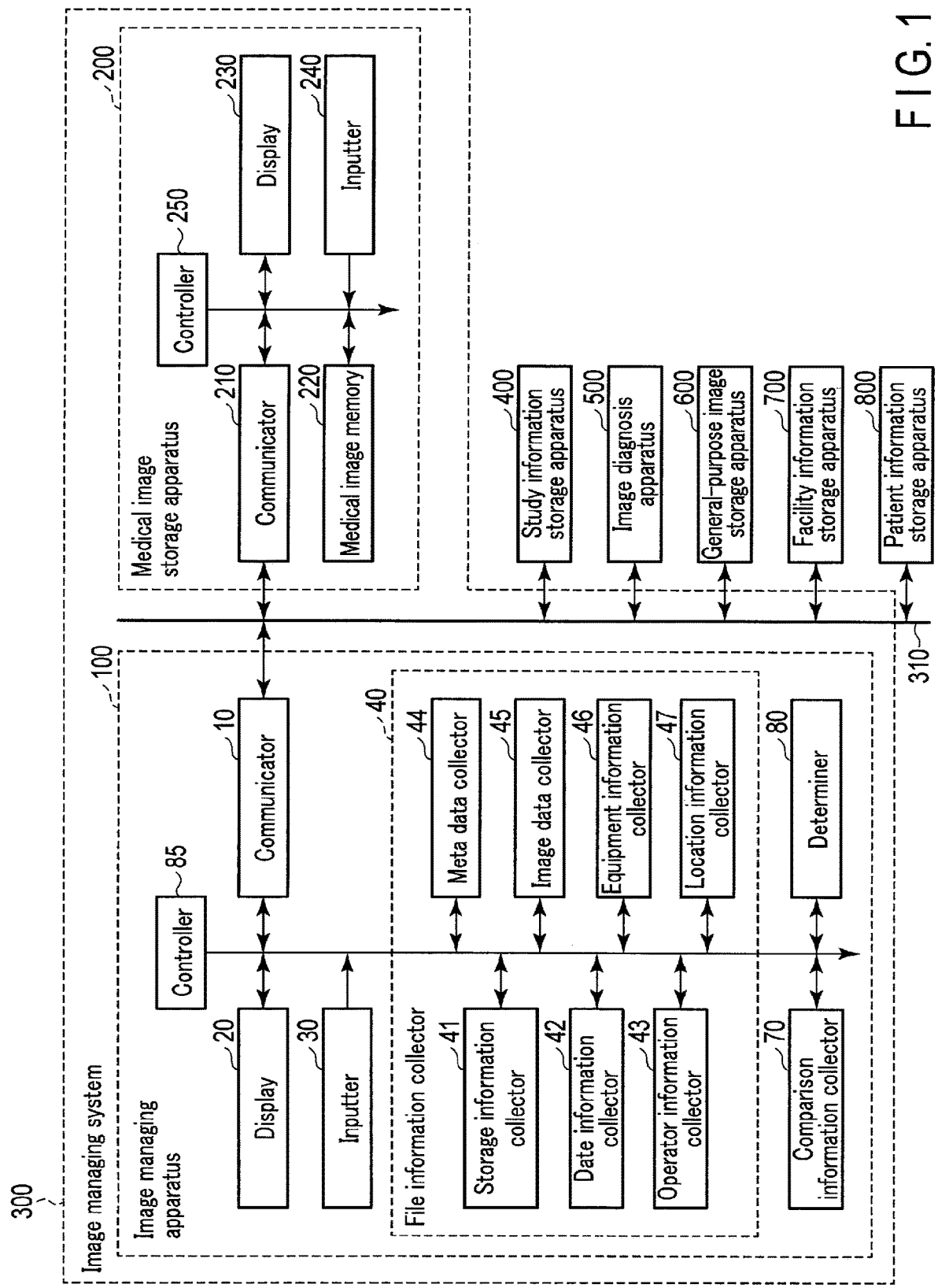
FIG. 1 is a function block diagram showing an example of a medical image processing system according to the first embodiment.

FIG. 1 is a function block diagram showing an example of a medical image processing system according to the first embodiment. An image managing system 300 (which is an example of a medical image processing system) comprises an image managing apparatus 100 (which is an example of a medical image processing apparatus) and a medical image storage apparatus 200. The image managing apparatus 100 and the medical image storage apparatus 200 are connected to each other via a network 310. A study information storage apparatus 400, an image diagnosis apparatus 500, a general-purpose image storage apparatus 600, a facility information storage apparatus 700 and a patient information storage apparatus 800 are also connected to the network 310.

The medical image storage apparatus 200 is configured to store medical image data compatible with the DICOM. The medical image data includes medical image data generated in the study using the image diagnosis apparatus 500, and study information attached to the medical image data. In the description set forth below, the data including both the medical image data and the study information will be referred to as DICOM image data. A medical image that can be displayed is prepared from the medical image data included in the DICOM image data.

The general-purpose image storage apparatus 600 is configured to store general-purpose image data that is not compatible with the DICOM. The image managing apparatus 100 manages how the general-purpose image data stored in the general-purpose image storage apparatus 600 is handled.

The study information storage apparatus 400 is configured to store study information. The study information is generated by information managing systems such as a Hospital Information System (HIS) and a Radiology Information System (RIS). The study information is generated for each of the studys carried out in a medical treatment facility. The study information includes, for example, study IDs for identifying individual studys, patient IDs for identifying the full names of subjects (names or patient names) and enabling the full names to be sorted according to the kind of study and sex, information representing the dates of study, etc.

The image diagnosis apparatus 500 is a modality such as an X-ray diagnosis apparatus, an X-ray CT apparatus, an MRI apparatus, a nuclear medical diagnosis apparatus or an endoscope apparatus. Each of these modalities can generate DICOM image data.

The general-purpose image storage apparatus 600 is configured to store files each including general-purpose image data and attribute information attached to the general-purpose image data. The general-purpose image data is obtained in relation to the study carried out by the image diagnosis apparatus 500 and is generated by an apparatus different from the image diagnosis apparatus 500 (for example, by a digital camera or by an image scanner). The general-purpose image data is image data showing what cannot be checked based on the study information obtained by the image diagnosis apparatus 500 or what is hard to check based on that study information. The attribute information is information attached to each general-purpose image data and representing, for example, the dates when the general-purpose image data is generated.

The facility information storage apparatus 700 is configured to store facility information. The facility information includes operator names or IDs identifying the operators (e.g., doctors) engaged in the respective studys, and apparatus ID information. The apparatus ID information is used for identifying the individual apparatuses (such as image scanners) provided in the medical facility, and includes information representing the types of apparatus, the model numbers and product serial numbers. The facility information also includes information representing the positions where the apparatuses identified by equipment identification information are provided, and information related to the positions and sortable according to the kinds of study.

The patient information storage apparatus 800 is configured to store patient information. The patient information includes information representing the age, sex, height etc. of each patient, and is used for identifying each patient.

The image managing apparatus 100 comprises a communicator 10, a display 20, an inputter 30, a file information collector 40, a comparison information generator 70, a determiner 80, and a controller 85.

The communicator 10 communicates with each of the medical image storage apparatus 200, study information storage apparatus 400, general-purpose image storage apparatus 600, facility information storage apparatus 700 and patient information storage apparatus 800, via the network 310. With this structure, the image managing apparatus 100 obtains DICOM image data from the medical image storage apparatus 200, for example. The image managing apparatus 100 obtains study information from the study information storage apparatus 400. The image managing apparatus 100 obtains files including general-purpose image data from the general-purpose image storage apparatus 600. The image managing apparatus 100 obtains facility information from the facility information storage apparatus 700. The image managing apparatus 100 obtains patient information from the patient information storage apparatus 800.

The inputter 30 receives inputs used for displaying a medical image or general-purpose image on the display 20. The display 20 is configured to display images generated from the DICOM image data received from the medical image storage apparatus 200 or files received from the general-purpose image storage apparatus 600.

From the general-purpose image storage apparatus 600, the file information collector 40 collects information related to the file including the general-purpose image data designated by the user. The comparison information generator 70 generates comparison information based on the information collected by the file information collector 40. In the descriptions below, the information used for comparison purpose will be referred to as "comparison information."

The determiner 80 determines whether or not the general-purpose image data obtained from the general-purpose image storage apparatus 600 and designated by the user is related to the study identified by the study information obtained from the medical image storage apparatus 200. In other words, the determiner 80 determines whether or not the general-purpose image data designated by the user is related to the DICOM image data obtained from the medical image storage apparatus 200. This determination is made based on the comparison information generated by the comparison information generator 70.

The controller 85 controls the image managing apparatus 100, including the communicator 10, display 20, file information collector 40, comparison information generator 70 and determiner 80.

The file information collector 40 collects file information. The file information includes various kinds of information relating to a file including general-purpose image data. The file information collector 40 comprises a storage information collector 41, a date information collector 42, an operator information collector 43, a metadata collector 44, an image data collector 45, an equipment information collector 46 and a location information collector 47.

The storage information collector 41 collects storage information. The storage information includes a model ID used for identifying the general-purpose image storage apparatus 600 in which files are stored, and folder (directory) information indicating where in the general-purpose image storage apparatus 600 the files are stored.

The date information collector 42 collects information on the dates included in the attribute information attached to the general-purpose image data of files. The operator information collector 43 collects operator IDs included in the attribute information of the files.

The metadata collector 44 collects metadata of the general-purpose image data designated by operating the inputter 30. The metadata is data attached to the corresponding general-purpose image data and indicates, for example, "pathological examination", "biopsy", "operative field image", etc. The image data collector 45 collects letters and numbers included in the general-purpose image data by image recognition technology.

The equipment information collector 46 collects equipment discrimination information included in the attribute information of files. The equipment discrimination information is information on the model and product serial number of the apparatus (image scanner) that generates the general-purpose image data.

The location information collector 47 collects location information included in the attribute information of files. The location information is, for example, information representing the location where the general-purpose image data is generated by a camera. Based on the collected location information, the location information collector 47 computes where the general-purpose image data of the files is generated (for example, the location of an operating room, the location of a pathology laboratory, the location of a CT examination room or the location of an MRI examination room).

Where the storage information collected by the storage information collector 41 includes name information, the comparison information generator 70 recognizes the name information and generates a patient name for comparison. In addition, the comparison information generator 70 generates an examination date for comparison from the dates collected by the date information collector 42. Further, the comparison information generator 70 generates an operator name for comparison based on the operator names and operator IDs obtained from the facility information storage apparatus 700 and the operator IDs collected by the operator information collector 43.

Still further, the comparison information generator 70 generates a "kind of study" based on the metadata collected by the metadata collector 44. If the metadata indicates pathological examination, the comparison information generator 70 generates "pathological diagnosis of tissue" as a kind of study for comparison. If the metadata indicates a biopsy, the comparison information generator 70 generates "living tissue diagnosis" as a kind of study for comparison. If the metadata indicates an operative field image, the comparison information generator 70 generates "surgical operation" as a kind of study for comparison.

The comparison information generator 70 prepares comparison information from the information collected by the image recognition processing performed by the image data collector 45. In addition, the comparison information generator 70 generates a kind of study for comparison, based on the facility information obtained from the facility information storage apparatus 700 and the equipment discrimination information collected by the equipment information collector 46.

The comparison information generator 70 generates a kind of study for comparison, based on the location computed by the location information collector 47. If the location indicates an operating room, the comparison information generator 70 generates "operation" or "ultrasonic diagnosis during operation" as a kid of study for comparison. If the location indicates a pathology laboratory, the comparison information generator 70 generates "pathological diagnosis of tissue." If the location indicates a CT examination room or an MRI examination room, the comparison information generator 70 generates "CT examination" or "MRI examination."

The determiner 80 compares the comparison information prepared by the comparison information generator 70 with the study information obtained from the study information storage apparatus 400. If the comparison shows that the study information obtained from the study information storage apparatus 400 contains the same study information as the comparison information, then the determiner 80 determines that the general-purpose image data designated by the user is related to DICOM image data (or to the study identified by study information). If the comparison shows that the study information obtained from the study information storage apparatus 400 does not contain the same study information as the comparison information generated by the comparison information generator 70, then the determiner 80 determines that the general-purpose image data designated by the user is not related to DICOM image data (or to the study identified by study information).

The medical image storage apparatus 200 comprises a communicator 210, a medical image memory 220, a display 230, an inputter 240 and a controller 250. The communicator 210 receives DICOM image data from the image diagnosis apparatus 500 by way of the network 310. The medical image memory 220 stores the DICOM image data received by the communicator 210. The display 230 displays a medical image corresponding to the DICOM image data stored in the medical image memory 220. The inputter 240 receives input information used for displaying a medical image or a general-purpose image on the display 230. The controller 250 controls the communicator 210, medical image memory 220 and display 230, based on the input information.

FIG. 2 shows an example of a list of study information stored in the study information storage apparatus 400. The study information list 402 has a plurality of columns, including "study ID", "kind", "patient ID", "patient name", "date of study" and "operator name."

In the "study ID" column, the study ID issued for each study is recorded. In the "kind" column, the kind of study identified by the study ID of the "study ID" column is recorded. In the "patient ID" column, patient ID for identifying the subject for which the study identified by the study ID of the "study ID" column is performed is recorded. In the "patient name" column, the name of the subject undergoing the study identified by the study ID of the "study ID" column is recorded.

In the "date of study" column, the date when the study identified by the study ID recorded in the "study ID" column is performed (i.e., the date of study) is recorded. In the "operator name" column, the operator who performs the study identified by the study ID of the "study ID" column is recorded.

In FIG. 2, "168" and "401" are shown as patient IDs. The patient identified by the patient ID "168" is Mr. Joe Smith, and the patient identified by the patient ID "401" is Mr. Taro Yamada.

From FIG. 2, it can be seen that Mr. Joe Smith underwent the X-ray examination identified by the study ID "10077" and the CT examination identified by the study ID "0123456" on the day indicated by "2014/Jan./10." The name of the operator concerning these examinations is "T.T."

From FIG. 2, it can also be seen that Mr. Joe Smith underwent the living tissue diagnosis identified by the study ID "4488" on the day indicated by "2014/Feb./25." The name of the operator concerning this diagnosis is "B.C."

The living tissue diagnosis is, for example, microscope observation of a disease tissue taken by a biopsy, or observation of image data on microscopic images. The image data captured for living tissue diagnosis (such as microscopic images) is data obtained by an apparatus different from the image diagnosis apparatus 500 and is therefore general-purpose image data.

From FIG. 2, it can be seen that Mr. Joe Smith underwent the surgical operation identified by the study ID "7555" on the day indicated by "2014/Mar./14" and underwent the pathological diagnosis of tissue identified by the study ID "1568" on the day indicated by "2014/Mar./15." The pathological diagnosis of tissue is microscope observation of a disease tissue removed at the time of the surgical operation, or observation of image data on microscopic images. The name of the surgeon is "Y.M", and the operator who made the pathological diagnosis is "T.M."

On the other hand, Mr. Taro Yamada underwent the MRI examination identified by the study ID "2266" on the day indicated by "2014/Jan./25." The name of the operator concerning this examination is "S.A."

Mr. Taro Yamada underwent the surgical operation identified by the study ID "7556" on the day indicated by "2014/Mar./16." The name of the surgeon is "A.D."

The study identified by the study ID "10077" is X-ray examination, and DICOM image data including study information is generated in the X-ray examination. The DICOM image data is stored in the medical image memory 220 of the image data storage apparatus 200. The study identified by the study ID "0123456" is CT examination, and DICOM image data including study examination is generated in the CT examination. The DICOM image data is stored in the medical image memory 220 of the image data storage apparatus 200. Similarly, the study identified by the study ID "2266" is MRI examination, and DICOM image data including study information is generated in the MRI examination. The DICOM image data is stored in the medical image memory 220 of the image data storage apparatus 200.

A description will now be given of an operation of the image managing apparatus 100 having the structure mentioned above.

The user operates the inputter 30 of the image managing apparatus 100 to display a list of the study information stored in the medical image storage apparatus 200. In response to this, the image managing apparatus 100 controls the display 20 to display a list of study information. When desired study information is designated, the controller 85 controls the display 20 to show the designated study information and a medical image of the DICOM image data corresponding to the study information.

Figure 3:
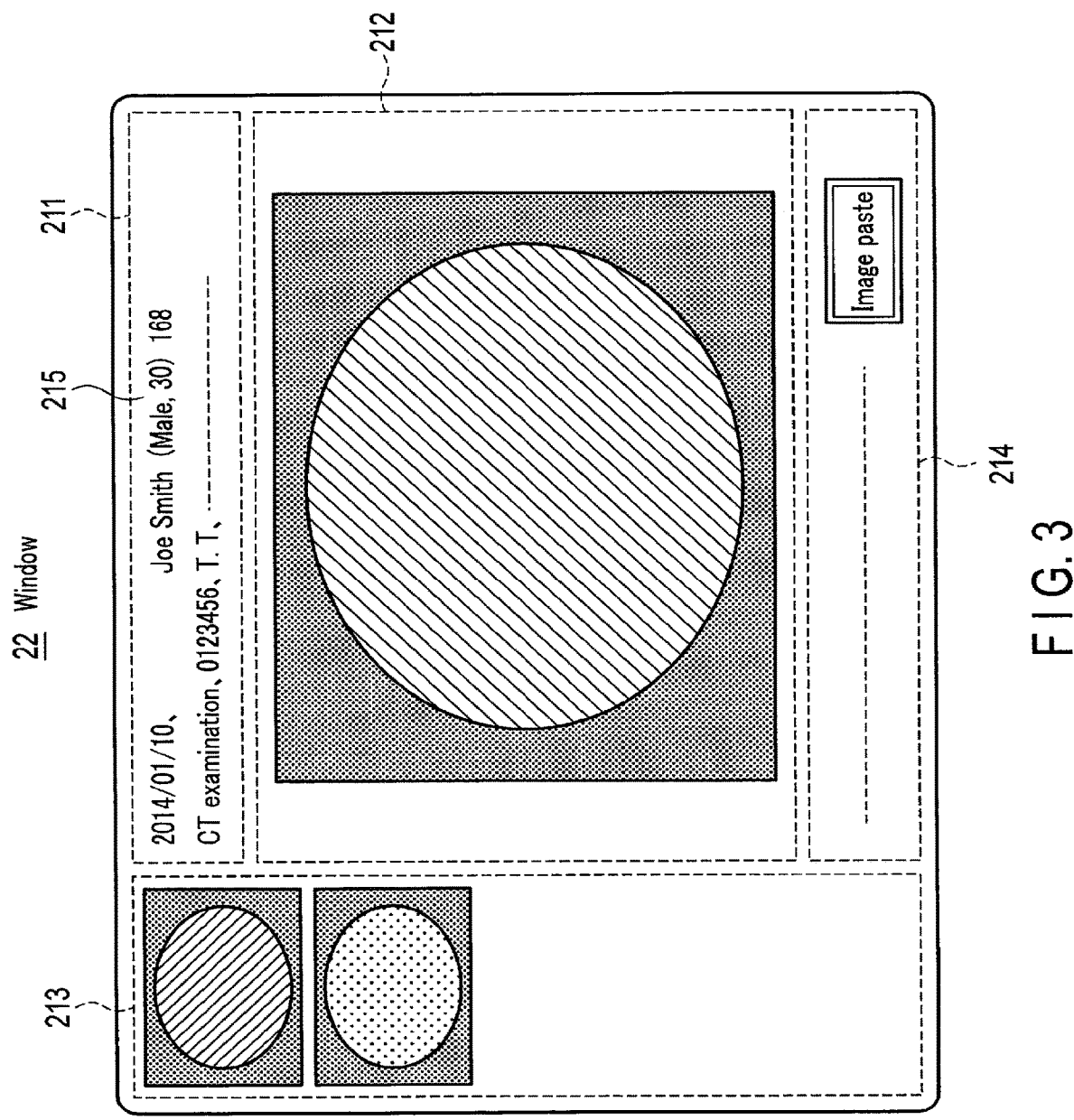
FIG. 3 shows an example of a window used for displaying medical information.

FIG. 3 shows an example of a window used for displaying medical information. The window 22 includes a first display area 211, a second display area 212, a third display area 213 and a fourth display area 214.

In the first display area 211, the study information 215 is displayed, which is attached to the DICOM image data of the medical image to be displayed in the second display area 212. The study ID of the study information displayed in the first display area 211 is "0123456." The operator name of this study is "T.T", the kind of study is "CT examination", the date of study is "2014/Jan./10", and the patient name (sex, age) and the patient ID are "Joe Smith (male, 30) 168." The study information 215 corresponds to the study information which has the study ID "0123456" in the study information list 402 shown in FIG. 2.

In the second display area 212, the medical image corresponding to the DICOM image data designated by the user is displayed. The designated DICOM image data is read from the medical image memory 220 of the medical image storage apparatus 200. The study information attached to the image data corresponding to the image displayed in the second display area is read from the study information storage apparatus 400 and displayed in the first display area 211.

Images related to the study information 215 are displayed in the third display area 213 as well. In the third display area 213, those images which are related to the study information 215 but are not designated by the user are displayed as reduced-size images (thumbnail images). Typically, there are a number of images corresponding to the study information 215. When one of the thumbnail images is designated, the designated image is enlarged to the original size and displayed in the second display area 212.

A clickable operation button or the like is displayed in the fourth display area 214. In the example shown in FIG. 3, an "image paste" button is shown. The "image paste" button is used for notifying the system of the start of the operation of associating general-purpose image data with the image displayed in the second display area 212.

The operation of associating the general-purpose image data with the image displayed in the second display area 212 is the same as the operation of associating the general-purpose image data with the study information shown in the first display area 211. However, there has been no technique available for confirming whether the general-purpose image data and the image data (or study information) associated therewith correctly correspond to each other. A description will now be given of a novel technique for confirmation.

When the "image paste" button shown in FIG. 3 is clicked, the user is urged to designate general-purpose image data. Using the directory hierarchy, the user looks for a folder in which the general-purpose image data designated by the user is stored. When the user reaches the folder, a window such as that shown in FIG. 4 is opened.

For example, when the general-purpose image storage apparatus 600 is designated as an apparatus for storing general-purpose image data, the communicator 10 obtains a list of folders from the general-purpose image storage apparatus 600 by way of the network 310. As a result, the list of folders is displayed on the display 20. For example, when a folder containing the same patient name as that of the study information 215 is designated, the communicator 10 obtains files (general-purpose image data) included in the designated folder from the general-purpose image storage apparatus 600. The files, thus obtained, are displayed on the display 20 as images. Next, the user performs an operation for designating general-purpose image data to be pasted.

Figure 4:
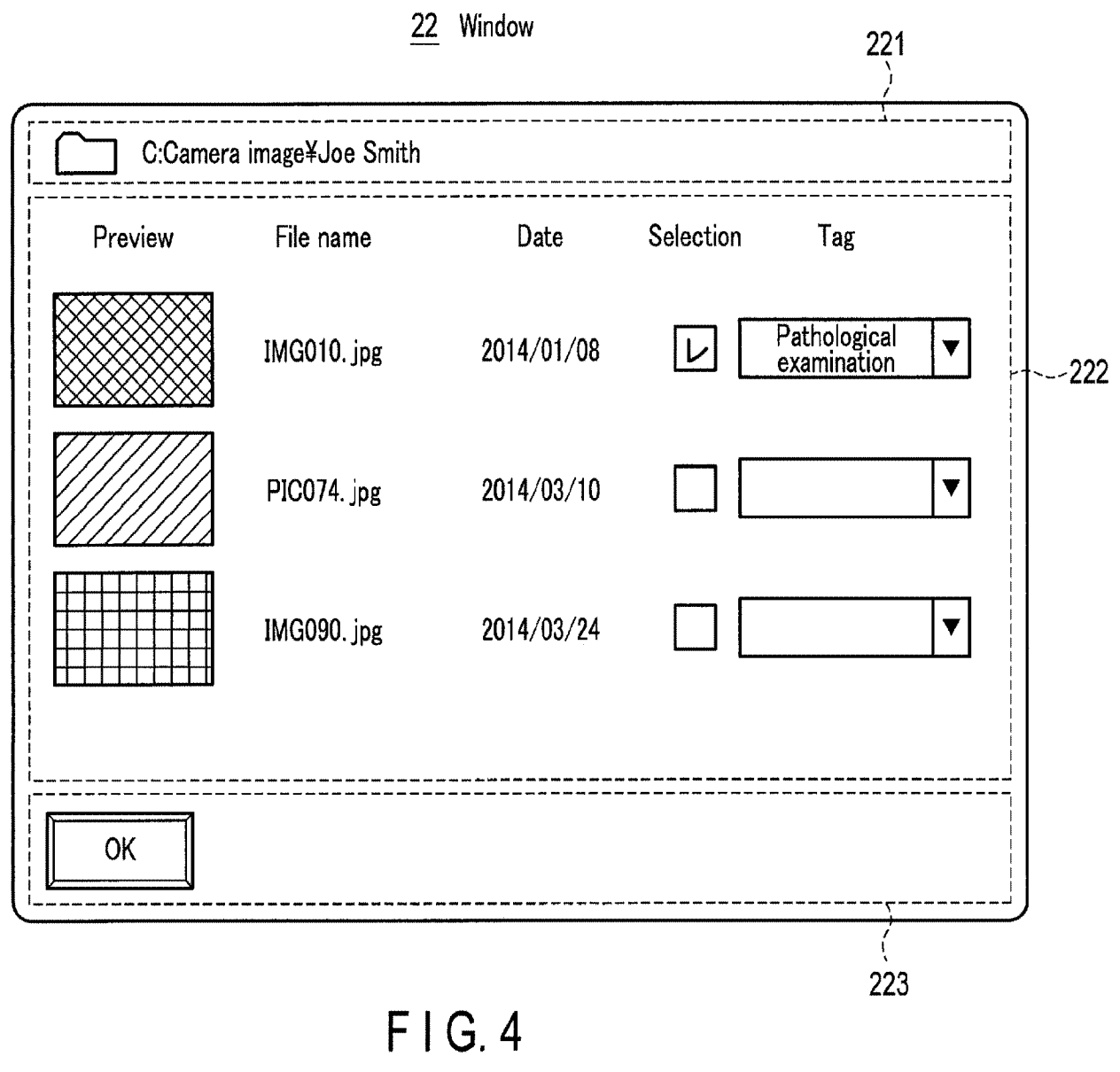

FIG. 4 shows an example of a user interface used for designating general-purpose image data. The window shown in FIG. 4 includes a first display area 221, a second display area 222 and a third display area 223. An "OK" button, which is an operation button for notifying the system of the user's operations, is displayed in the third display area 223.

A current folder and its path information are displayed in the first display area 221. FIG. 4 shows that the path of the current folder is "C:Camera Image\Joe Smith." "Camera Image" is a folder name indicating that general-purpose image data captured by a digital camera are stored. "Joe Smith" is a folder name indicating a patient name. In a system operating on Windows (registered trademark), general-purpose image data on Mr. Joe Smith is stored in the "Joe Smith" folder of the "Camera Image" folder directly under the C drive.

The general-purpose image data files stored in the current folder are displayed in the second display area 222 as thumbnail images. The second display area 222 includes a "preview" column, a "file name" column, a "date" column, a "section" column and a "tag" column.

The thumbnail images of, for example, three general-purpose image data are displayed in the "preview" column. More thumbnail images can be displayed by vertically sliding a scroll bar (not shown).

The file names corresponding to the thumbnail images are displayed in the "file name" column. In FIG. 4, the file names are, from top down, "IMG010.jpg", "PIC074.jpg" and "IMG090.jpg."

The dates when the corresponding thumbnail images are created are displayed in the "date" column. In FIG. 4, the creation dates of the files are, from top down, "2014/Jan./8", "2014/Mar./10" and "2014/Mar./24."

Check boxes corresponding to the respective files are displayed in the "selection" column. When a check box is clicked, a check mark indicating that the corresponding file is selected (or designated) is displayed. Dialog boxes corresponding to the respective files and indicating the kinds of general-purpose image data being previewed are displayed in the "tag" column. Attribute information such as "pathological examination", "biopsy" and "operative field image" can be designated using a drop-down list. The designated attribute information is attached to the corresponding file as metadata.

For example, when the user checks the check box of "IMG010.jpg", designates "pathological examination" as attribution information of the file and clicks the "OK" button, the window 22 is closed. This state is a state where "IMG010.jpg" is associated with the study identified by the study information 215 (FIG. 3).

The file information collector 40 collects file information including metadata regarding the designated file ("IMG010.jpg"). The comparison information generator 70 prepares comparison information based on the collected file information (including metadata) and the facility information obtained from the facility information storage apparatus 700.

FIG. 5A shows an example of file information. The file information indicated by 401 includes "folder/file", "date", "operator ID" and "metadata." The "folder/file" is storage information of "IMG010.jpg" collected by the storage information collector 41. The "folder/file" includes "C:Camera Image/Joe Smith", which is the storage location of "IMG010.jpg", and "IMG010", which is the base name of "IMG010.jpg." The date of "IMG010.jpg" is "2014/Jan./8 14:16:25."

The "operator ID" is an operator ID included in the attribute information collected by the operator information collector 43. The "operator ID" of "IMG010.jpg" is "p9876543." The "metadata" is metadata collected by the metadata collector 44. The "metadata" of "MG010.jpg" is "pathological examination."

FIG. 5B shows an example of comparison information prepared based on the file information depicted in FIG. 5A.

The comparison information indicated by 71 includes "patient name", "date of study", "operator name" and "kind of study." The "patient name" is supposed from the "folder/file" of the file information 401. Since the "folder/file" includes "C:Camera Image\Joe Smith", the patient name is supposed to be "Joe Smith."

The "date of study" is supposed from the dates collected by the date information collector 42. In FIG. 5A, the date of study of the comparison information 71 is supposed to be "2014/Jan./8." The "operator name" is supposed from the operator IDs collected by the operator information collector 43. The "operator ID" shown in FIG. 5A is "p9876543." The operator name of the comparison information 71 is supposed to be "S.Y" based on a comparison table of operator IDs and operator names, which table is prepared beforehand. The "kind of study" is supposed from the metadata collected by the metadata collector 44. The metadata shown in FIG. 5A indicates pathological examination, and "pathological diagnosis of tissue" is supposed as the kind of study of the comparison information 71.

The determiner 80 determines whether the general-purpose image data designated using the window shown in FIG. 4 is related to the medical image (DICOM image data) shown in FIG. 3, based on the study information 215 (FIG. 3) attached to the medical image and the comparison information 71. If the study information 215 contains information identical to the patient name, the date of study, the operator name and the kind of study of the comparison information 71, then the determiner 80 determines that the general-purpose image data is related to the associated medical image (DICOM image data). If the study information 215 does not contain information identical to the patient name, the date of study, the operator name or the kind of study of the comparison information 71, then the determiner 80 determines that the general-purpose image data is not related to the associated medical image (DICOM image data).

The patient name shown in FIG. 3 is the same as that shown in FIG. 5B, but the date of study shown in FIG. 3 is different from that shown in FIG. 5B. Therefore, the file information collector 40 collects study information, including patient name "Joe Smith" and its patient ID "168", from the study information storage apparatus 400. As a result, the study list related to patient ID "168" is generated.

FIG. 6 shows an example of a study list indicated by 81. If the study list 81 contains information identical to the date of study, the kind of study and the operator name of the comparison information 71, the determiner 80 determines that the general-purpose image data is related to the associated medical image (DICOM image data). In this case, the determiner 80 attaches the study information 215 to the file and outputs the resultant file to the communicator 10. The communicator 10 transmits the file, having the study information 215 attached thereto, to the medical image storage apparatus 200. The medical information storage apparatus 200 stores the file transmitted from the image managing apparatus 100 after associating it with the study information 215.

If the study list 81 does not contain information identical to the date of study, the kind of study or the operator name of the comparison information 71, the determiner 80 determines that the general-purpose image data is not related to the associated medical image (DICOM image data). The kind of study and the operator name of the study identified by study ID "1568" in the list 81 may be the same as those of the comparison information 71. However, since the date of study is different from the date of study of the comparison information 71, the comparison information 71 does not contain study information including the date of study, the kind of study or the operator name. Therefore, the determiner 80 determines that the general-purpose image data is not related to the DICOM image data of the study information 215, and displays a warning on the display 20.

FIG. 7 shows an example of a window 23 in which the warning is displayed. For example, the window 23 displays a warning mark, "WARNING", and the message "the image to be pasted may be that of an unrelated patient." The window 23 also displays comparison information and a list. The displayed comparison information includes the message "the study supposed from the image", the kind of study "pathological diagnosis of tissue", and the date "2014/Jan./

8." The displayed list includes the message "list of patients related to pasting" and the contents of the list 81.

As described above, the image managing apparatus 100 collects information on the storage location of the general-purpose image data, the metadata indicating the kind of input general-purpose image data, the date attached to the general-purpose image data, and the operator ID, and prepares comparison information 71 based on the collected information. The image managing apparatus 100 compares the comparison information 71 with the study information obtained from the study information storage apparatus 400. Based on the result of this comparison, the image managing apparatus 100 determines whether the general-purpose image data designated by the user is related to the study (or DICOM image data) identified by the study information 215. Owing to this, a determination can be made as to whether the general-purpose image data to be associated with the DICOM image data correctly corresponds to the DICOM image data. Accordingly, incorrect image association can be prevented.

If study information cannot be obtained from the study information storage apparatus 400, a determination as to whether the general-purpose image data and the DICOM image data (to which the general-purpose image data is to be paste) are related to each other can be made based on the study information stored in the medical image memory 220. In this case, the file information collector 40 collects file information excluding metadata from the file information shown in FIG. 5A.

FIG. 8A shows another example of file information. Unlike file information 401 mentioned above, this file information 401a does not contain metadata.

FIG. 8B shows an example of comparison information prepared based on the file information depicted in FIG. 8A. The comparison information generator 70 prepares comparison information 71a by excluding the "kind of study" item from the comparison information 71 shown in FIG. 5B.

If the information other than the date of study of the comparison information 71a is the same as the study information 215, and the date of study of the comparison information 71a is within an allowable range predetermined based on the date of study of the study information 215, then the determiner 80 determines that the general-purpose image data and the DICOM image data (to which the general-purpose image data is to be pasted) are related to each other. If the information other than the date of study of the comparison information 71a is not the same as the study information 215, or the date of study of the comparison information 71a is not within the allowable range predetermined based on the date of study of the study information 215, then the determiner 80 determines that the general-purpose image data and the DICOM image data (to which the general-purpose image data is to be pasted) are not related to each other.

As described above, the image managing apparatus 100 collects the storage locations of the general-purpose image data, the dates attached to the general-purpose image data, and the operator IDs, and generates comparison information 71a based on the collected information. In addition, the image managing apparatus 100 can determine whether the general-purpose image data designated by the user correctly corresponds to the DICOM image data with which it is associated, based on the comparison information 71a and the date of study included in the study information. Accordingly, incorrect image association can be prevented.

FIG. 9 shows another example of a window used for displaying a medical image. The user operates the inputter 30 to display a list of the study information stored in the medical image memory 220. In response to this, the image managing apparatus 100 controls the display 20 to display a list of study information. When desired study information is designated, the controller 85 controls the display 20 to show a window 21a (FIG. 9) including the designated study information and the DICOM image data corresponding to the study information.

In the window 21a, the study information on Mr. Taro Yamada is displayed in the first display area 211. The study ID of the study information 215a is "2266." The operator name of this study is "S.A", the kind of study is "MRI examination", the date of study is "2014/Jan./25", and the patient name (sex, age) and the patient ID are "Taro Yamada (male, 45) 401." The study information 215a corresponds to the study information which has the study ID "2266" in the study information list 402 shown in FIG. 2.

When the "image paste" button shown in FIG. 9 is clicked, the user is urged to designate general-purpose image data. Using the directory hierarchy, the user looks for a folder in which the general-purpose image data designated by the user is stored. When the user reaches the folder, a window such as that shown in FIG. 10 is opened.

For example, when the general-purpose image storage apparatus 600 is designated as an apparatus for storing general-purpose image data, the communicator 10 obtains a list of folders from the general-purpose image storage apparatus 600 by way of the network 310. As a result, the list of folders is displayed on the display 20. For example, when a "scan image" folder is designated from the list of folders, the communicator 10 obtains files (general-purpose image data) included in the designated folder from the general-purpose image storage apparatus 600. The files, thus obtained, are displayed on the display 20 as images. Next, the user performs an operation for designating general-purpose image data to be pasted.

Figure 10:
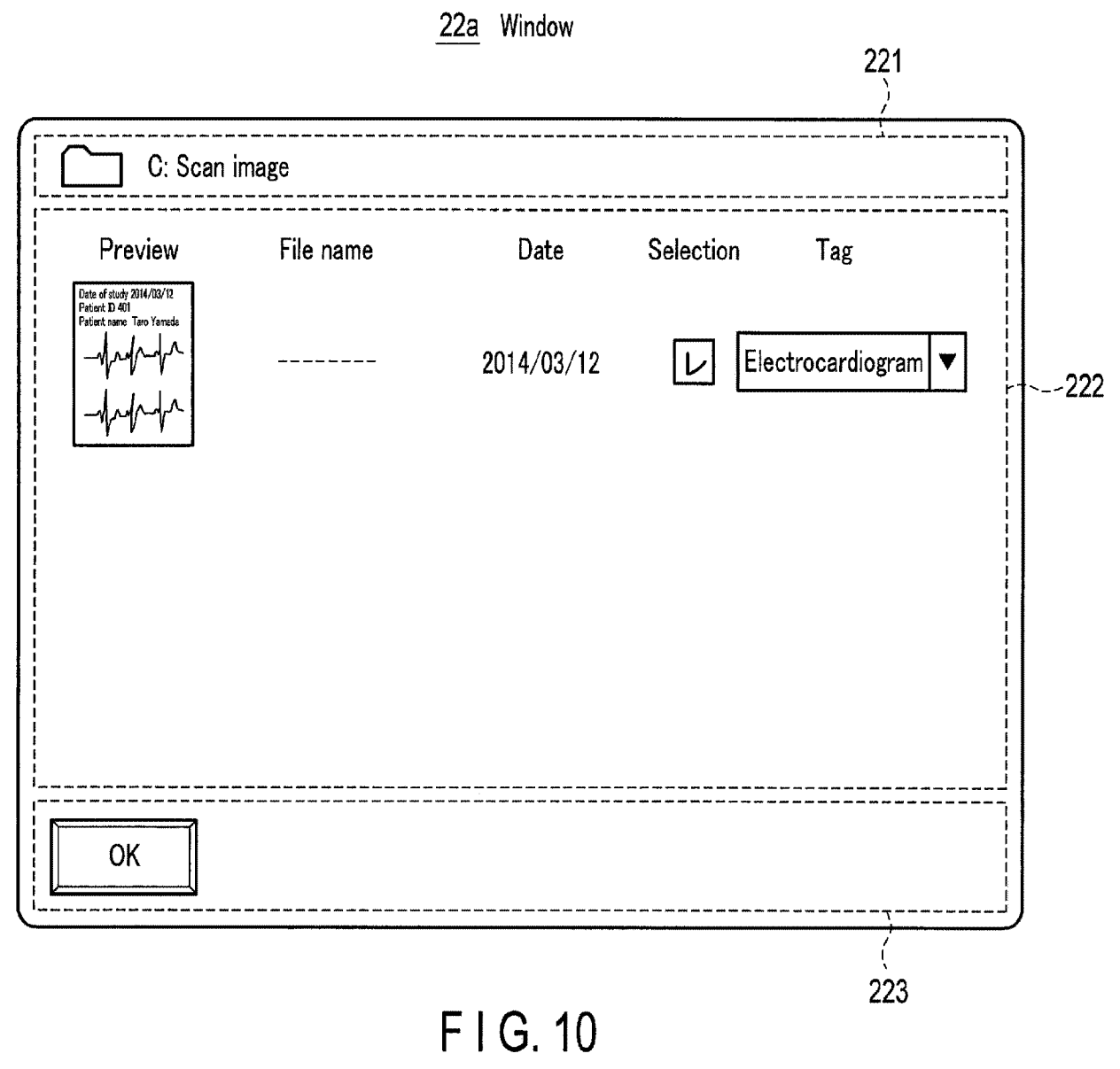

FIG. 10 shows another example of a user interface used for designating general-purpose image data. A current folder and its path information are displayed in the first display area 221. FIG. 10 shows that the path of the current folder is "C:Scan Image." The "Scan Image" is a folder name indicating that general-purpose image data captured by an image scanner are stored. In a system operating on Windows (registered trademark), general-purpose image data is stored in the "Scan Image" folder directly under the C drive.

The general-purpose image data files stored in the current folder are displayed in the second display area 222 as thumbnail images. In the second display area 222, information similar to that shown in FIG. 4 is displayed. For example, when the user checks the check box, designates "electrocardiogram" in a drop-down list, and clicks the "OK" button, the window 22 is closed. When the user performs the operation for designating image recognition, the window 21a appears again on top of the display 20. When the "image paste" button on the window 21a is clicked, the file information collector 40 collects file information on the designated file.

FIG. 11 shows an example of general-purpose image data captured by an image scanner. The general-purpose image data 51 includes waveforms (electrocardiogram) and the study information on the electrocardiogram, such as "date of study", "patient ID" and "patient name." In FIG. 11, the date of study is "2014/Mar./12", the patient ID is "401" and the patient name is "Taro Yamada."

The file information collector 40 collects symbols included in the general-purpose image data by image recognition of the general-purpose image data 51. The comparison information generator 70 generates comparison information based on the file information including the symbols collected by the file information collector 40.

In the case where the storage information collected by the storage information collector 41 includes a scan image, file information may be collected by controlling the image data collector 45 to execute image recognition.

FIG. 12A shows another example of file information. The file information 401b includes symbols recognized by image recognition. The file information 401b includes "folder/file", "date of study", "patient ID", "patient name" and "metadata."

The "folder/file" is storage information collected by the storage information collector 41, and is a "scan image/ . . . " in the file information 401b. The "date of study", "patient ID" and "patient name" are symbols collected by the image data collector 45. The date of study in the file information 401b is "2014/Mar./12." The patient ID in the file information 401b is "401." The patient name in the file information 401b is "Taro Yamada." The metadata is collected by the metadata collector 44. The metadata in the file information 401b is "electrocardiogram."

FIG. 12B shows an example of comparison information prepared based on the file information depicted in FIG. 12A. The comparison information 71b includes the date of study, client ID and client name which are supposed based on the information collected by the image data collector 45, and the kind of study which is supposed based on the information collected by the metadata collector 44. The date of study, patient ID, patient name and kind of study of the comparison information 71b are "2014/Mar./12", "401", "Taro Yamada" and "electrocardiogram examination", respectively.

Based on the comparison information 71b, the determiner 80 determines whether the general-purpose image data 51 (FIG. 11) is related to the study identified by the study information 215a (FIG. 9), i.e., the medical image displayed in the second display area 212. If the study information obtained from the study information storage apparatus 400 contains information identical to the date of study, the patient ID, the patient name and the kind of study of the comparison information 71b, the determiner 80 determines that the general-purpose image data 51 is related to the study identified by study information 215a. If the study information obtained from the study information storage apparatus 400 does not contain information identical to the date of study, the patient ID, the patient name or the kind of study of the comparison information 71b, the determiner 80 determines that the general-purpose image data 51 is not related to the study identified by study information 215a.

In the case where the study information storage apparatus 400 stores a large amount of study information, study information may be obtained from the study information storage apparatus 400 by designating a period of dates of studies and thereby excluding obviously old study records.

As described above, the comparison information 71b can be prepared based on the information obtained by image recognition of general-purpose image data and the information on the storage location of the general-purpose image data. The comparison information 71b and the study information obtained from the study information storage apparatus 400 are compared with each other. Based on the result of this comparison, a determination can be made as to whether or not the designated general-purpose image data is related to the study identified by the study information. Accordingly, incorrect image association can be prevented.

Figure 13:
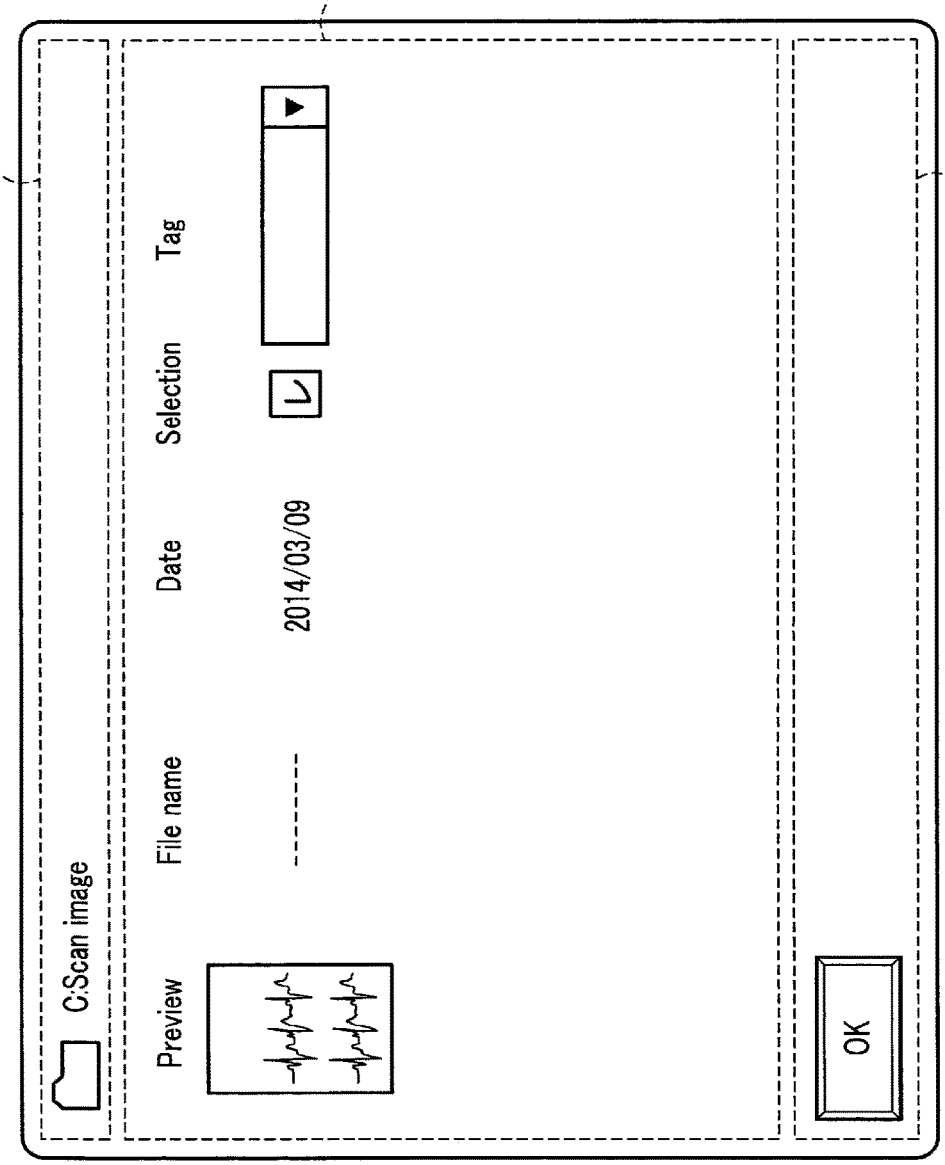
FIG. 13 shows another example of a user interface used for designating general-purpose image data.

FIG. 13 shows another example of a user interface used for designating general-purpose image data. In the window 22b shown in FIG. 13, the path of the current folder is "C:Scan Image." The "Scan Image" indicates that general-purpose image data is data captured by an image scanner. The equipment identification information of the image scanner can be attached to the general-purpose image data.

In the second display area 222, information similar to that shown in FIG. 10 is displayed. The blank dialog box in the tag column indicates that there is no metadata. When the "OK" button is clicked, window 22b is closed, and window 21a (FIG. 9) appears on top of the display 20. When the "image paste" button on window 21a is clicked, the file information collector 40 collects file information on the designated file. This file information includes equipment identification information. The comparison information generator 70 generates comparison information based on the file information collected by the file information collector 40.

FIG. 14A shows another example of file information. The file information indicated by 401c includes "folder/file", "date", "model" and "product serial number." The "folder/file" is storage information collected by the storage information collector 41, and is a "scan image/ . . . " in the file information 401c.

The "date" is collected by the date information collector 42 and indicates the date of scan. The date in the file information 401c is "2014/Mar./9 14:11:52." The "model" is equipment identification information collected by the equipment information collector 46. The model in the file information 401c is "TC copy/scanner." The "product serial number" is a serial number collected by the equipment information collector 46. The product serial number in the file information 401c is "9998876."

FIG. 14B shows an example of comparison information prepared based on the file information depicted in FIG. 14A. The comparison information 71c includes "date of study" and "kind of study." The "date of study" is supposed from the dates collected by the date information collector 42. The date of study in the comparison information 71c is "2014/ Mar./9." The "kind of study" is supposed from the equipment identification information collected by the equipment information collector 46. Since the kind of study supposed from "TC copy/scanner" is electrocardiogram examination, this is reflected in the comparison information 71c as well.

Based on the comparison information 71c, the determiner 80 determines whether the general-purpose image data 51 shown as a thumbnail image (FIG. 13) in window 22b is related to the study identified by the study information 215a (FIG. 9).

If the study information obtained from the study information storage apparatus 400 contains information identical to the date of study and the kind of study of the comparison information 71c, the determiner 80 determines that the general-purpose image data 51 is related to the study identified by study information 215a. If the study information obtained from the study information storage apparatus 400 does not contain information identical to the date of study or the kind of study of the comparison information 71c, the determiner 80 determines that the general-purpose image data 51 is not related to the study identified by study information 215a.

As described above, the date information attached to the general-purpose image data and the location information are collected, and comparison information 71c can be generated based on the collected information. The comparison information 71c and the study information obtained by the study information storage apparatus 400 are compared with each other. Based on the result of this comparison, a determination can be made as to whether or not the designated general-purpose image data is related to the study identified by the study information. Accordingly, incorrect image association can be prevented.

Where the metadata of the general-purpose image data 51 includes patient IDs and patient names, the image data collector 45 may collect them and include them in the comparison information 71c. In this case, if the study information obtained from the study information storage apparatus 400 contains information identical to the date of study, the kind of study, the patient ID and the patient name of the comparison information 71c, the determiner 80 determines that the general-purpose image data 51 is related to the study identified by study information 215a. Conversely, if the study information obtained from the study information storage apparatus 400 does not contain information identical to the date of study, the kind of study, the patient ID or the patient name of the comparison information 71c, the determiner 80 determines that the general-purpose image data 51 is not related to the study identified by study information 215a.

FIG. 15 shows another example of a user interface used for designating general-purpose image data. In the window 22c shown in FIG. 15, the path of the current folder is "C:Camera Image." "Camera Image" indicates that image data is captured by a digital camera, for example.

In the second display area 222, information similar to that shown in FIG. 13 is displayed. The blank dialog box in the tag column indicates that there is no metadata. When the "OK" button is clicked, window 22c is closed, and window 21a (FIG. 9) appears on top of the display 20. When the "image paste" button on window 21a is clicked, the file information collector 40 collects file information related to the designated file. This file information includes location information. The comparison information generator 70 generates comparison information based on the file information collected by the file information collector 40.

FIG. 16A shows another example of file information. The file information indicated by 401d includes "folder/file", "date", and "location information." The "folder/file" is storage information collected by the storage information collector 41, and is a "camera image/PIC065" in the file information 401c.

The "date" is information collected by the date information collector 42 and indicates the date of photography. The date in the file information 401d is "2014/Mar./8 15:12:34." The location information is a photography location calculated based on the location information collected by the location information collector 47. The location information in the file information 401d is an "operating room."

FIG. 16B shows an example of comparison information prepared based on the file information depicted in FIG. 16A. The comparison information 71d includes "date of study" and "kind of study." The "date of study" is supposed from the dates collected by the date information collector 42. The date of study in the comparison information 71c is "2014/Mar./8." The "kind of study" is supposed from the location information collected by the location information collector 47. Two kinds of study, namely "operation" and "ultrasonic diagnosis during operation", can be supposed from "operating room." This is reflected in the comparison information 71d.

Based on the comparison information 71d, the determiner 80 determines whether the general-purpose image data shown as a thumbnail image (FIG. 15) in window 22c is related to the study identified by the study information 215a (FIG. 9).

If the study information obtained from the study information storage apparatus 400 contains information identical to the date of study and the kind of study of the comparison information 71d, the determiner 80 determines that the designated general-purpose image data is related to the study identified by study information 215a. If the study information obtained from the study information storage apparatus 400 does not contain information identical to the date of study or the kind of study of the comparison information 71d, the determiner 80 determines that the designated general-purpose image data is not related to the study identified by study information 215a.

As described above, the date information attached to the general-purpose image data and the location information are collected, and comparison information 71d can be generated based on the collected information. The comparison information 71d and the study information obtained by the study information storage apparatus 400 are compared with each other. Based on the result of this comparison, a determination can be made as to whether or not the designated general-purpose image data is related to the study identified by the study information. Accordingly, incorrect image association can be prevented.

Second Embodiment

Figure 17:
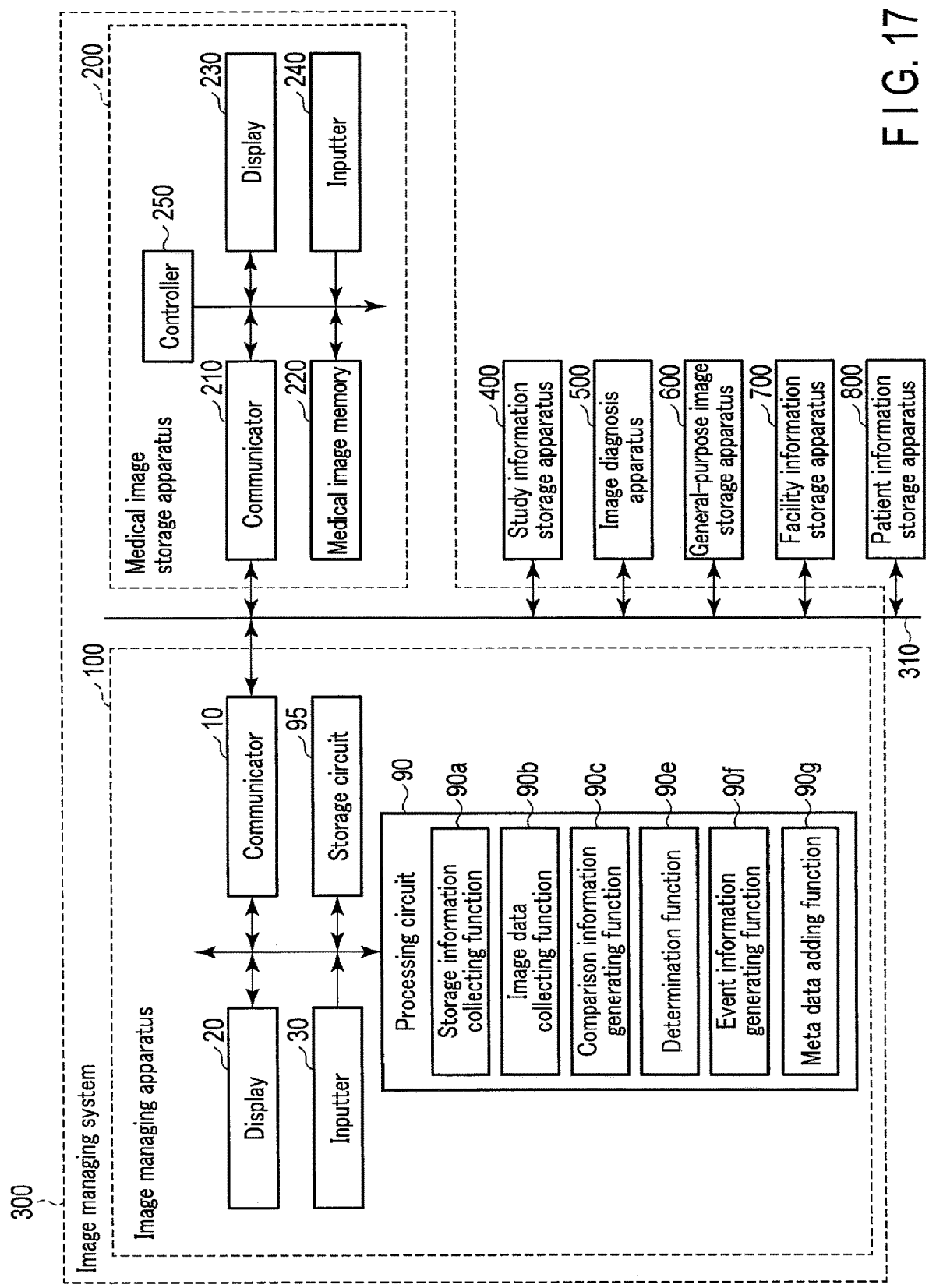
FIG. 17 is a function block diagram showing an example of a medical image processing system according to the second embodiment.

FIG. 17 is a function block diagram showing an example of a medical image processing system according to the second embodiment. In FIG. 17, elements similar or corresponding to those shown in FIG. 1 are denoted by the same reference symbols, and a repetitive description of such elements will be omitted.

Referring to FIG. 17, the image managing apparatus 100 comprises a communicator 10, a display 20, an inputter 30, a processing circuit 90, and a storage circuit 95.

The processing circuit 90 includes, for example, a processor and a memory. The processing circuit 90 functions as an information processing apparatus (a computer) and controls the image managing apparatus 100. The processing circuit 90 reads various programs (e.g., program 95a) related to control processing from the storage circuit 95. After reading program 95a, the processing circuit 90 has the functions shown in FIG. 17, namely a storage information collecting function 90a, an image data collecting function 90b, a comparison information generating function 90c, a determination function 90e, an event information generating function 90f and a metadata adding function 90g. In other words, the processing circuit 90 reads, from the storage circuit 95, programs related to the storage information collecting function 90a, the image data collecting function 90b, the comparison information generating function 90c, the determination function 90e, the event information generating function 90f and the metadata adding function 90g.

The processing circuit 90 loads the program related to the storage information collecting function in its memory, and executes the program to realize the storage information collecting function 90a. At the time, the processing circuit 90 functions as a storage information collector. The storage information collecting function 90a is a function of collecting storage information regarding general-purpose image data.

The processing circuit 90 loads the program related to the image data collecting function in its memory, and executes the program to realize the image data collecting function 90b. At the time, the processing circuit 90 functions as an image data collector. The image data collecting function 90b is a function of collecting appendant data pertaining to general-purpose image data. The appendant data is, for example, data attached to an image file having a format known as Exchangeable image file format (Exif). Examples of the appendant data include the date of photography of an image file, the vendor name of a photographing unit, the type of photographing unit, the photographing time, position information (such as global positioning system (GPS) data), a thumbnail, etc.

The processing circuit 90 loads the program related to the comparison information generating function in its memory, and executes the program to realize the comparison information generating function 90c. At the time, the processing circuit 90 functions as a comparison information generator. The comparison information generating function 90c is a function of generating comparison information based on the storage information collected by the storage information collecting function 90a, the appendant data collected by the image data collecting function 90b, event information and metadata.

The processing circuit 90 loads the program related to the determination function in its memory, and executes the program to realize the determination function 90e. At the time, the processing circuit 90 functions as a determiner. The determination function 90e is a function of determining whether general-purpose image data is related to the study in which DICOM image data is prepared, based on the comparison information prepared by the comparison information generating function 90c.

The processing circuit 90 loads the program related to the event information creating function in its memory, and executes the program to realize the event information creating function 90f. At the time, the processing circuit 90 functions as an event information creator. The event information creating function 90f is a function of creating event information related to the study in which the DICOM image data is prepared.

The processing circuit 90 loads the program related to the metadata adding function in its memory, and executes the program to realize the metadata adding function 90g. At the time, the processing circuit 90 functions as a metadata adder. The metadata adding function 90g is a function of adding, to general-purpose image data, metadata indicating what is indicated by the general-purpose image data. The metadata is added by adding information, for example, to the tag region of the general-purpose image data. What is indicated by the general-purpose image data (pathological examination, biopsy, operative field image, etc.) can be specified by referring to the attached metadata.

Owing to this feature, comparison information is prepared based on the storage information representing the storage location of general-purpose image data (such as a folder structure and information on a picture sharing server), the appendant data originally attached to the general-purpose image data, the event information, and the metadata. Therefore, the validity of the general-purpose image data can be checked based on not only the information regarding the study but also whether or not the appendant information on the events correlated with the study is relevant. Owing to this, a determination can be made as to whether the general-purpose image data to be associated with the DICOM image data correctly corresponds to the DICOM image data. Accordingly, incorrect image association can be prevented in the second embodiment as well.

Third Embodiment

Figure 18:
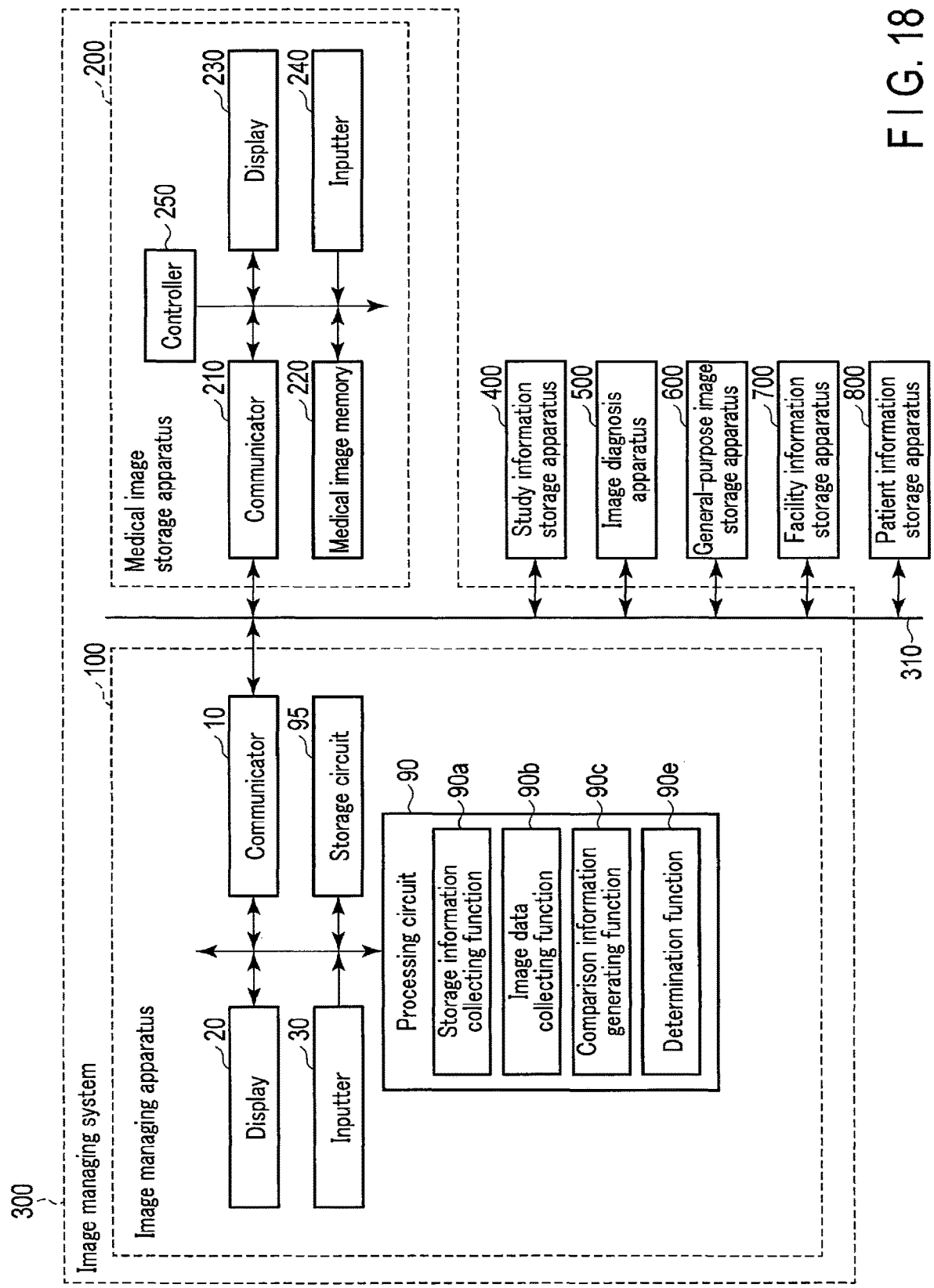
FIG. 18 is a function block diagram showing an example of a medical image processing system according to the third embodiment.

FIG. 18 is a function block diagram showing an example of a medical image processing system according to the third embodiment. In FIG. 18, elements similar or corresponding to those shown in FIG. 1 are denoted by the same reference symbols, and a repetitive description of such elements will be omitted.

After reading the program 95a, the processing circuit 90 has the functions shown in FIG. 18, namely, a storage information collecting function 90a, an image data collecting function 90b, a comparison information generating function 90c, and a determination function 90e. In other words, the processing circuit 90 reads, from the storage circuit 95, programs related to the storage information collecting function 90a, the image data collecting function 90b, the comparison information generating function 90c, and the determination function 90e.

The processing circuit 90 loads the program related to the storage information collecting function in its memory, and executes the program to realize the storage information collecting function 90a. At the time, the processing circuit 90 functions as a storage information collector. The storage information collecting function 90a is a function of collecting storage information regarding general-purpose image data.

The processing circuit 90 loads the program related to the image data collecting function 90b in its memory, and executes the program to realize the image data collecting function 90b. At the time, the processing circuit 90 functions as an image data collector. The image data collecting function 90b is a function of collecting appendant data pertaining to general-purpose image data.

The processing circuit 90 loads the program related to the comparison information generating function in its memory, and executes the program to realize the comparison information generating function 90c. At the time, the processing circuit 90 functions as a comparison information generator. The comparison information generating function 90c is a function of generating comparison information based on the storage information collected by the storage information collecting function 90a and the appendant data collected by the image data collecting function 90b.

The processing circuit 90 loads the program related to the determination function in its memory, and executes the program to realize the determination function 90e. At the time, the processing circuit 90 functions as a determiner. The determination function 90e is a function of determining whether general-purpose image data is related to the study in which DICOM image data is generated, based on the comparison information generated by the comparison information generating function 90c.

Owing to this feature, comparison information is generated based on the storage information representing the storage location of general-purpose image data and the appendant data originally attached to the general-purpose image data. Therefore, the validity of the general-purpose image can be checked in a simplified way. According to the third embodiment, a determination can be made as to whether the general-purpose image data to be associated with the DICOM image data correctly corresponds to the DICOM image data. Accordingly, incorrect image association can be prevented.

Fourth Embodiment

Figure 19:
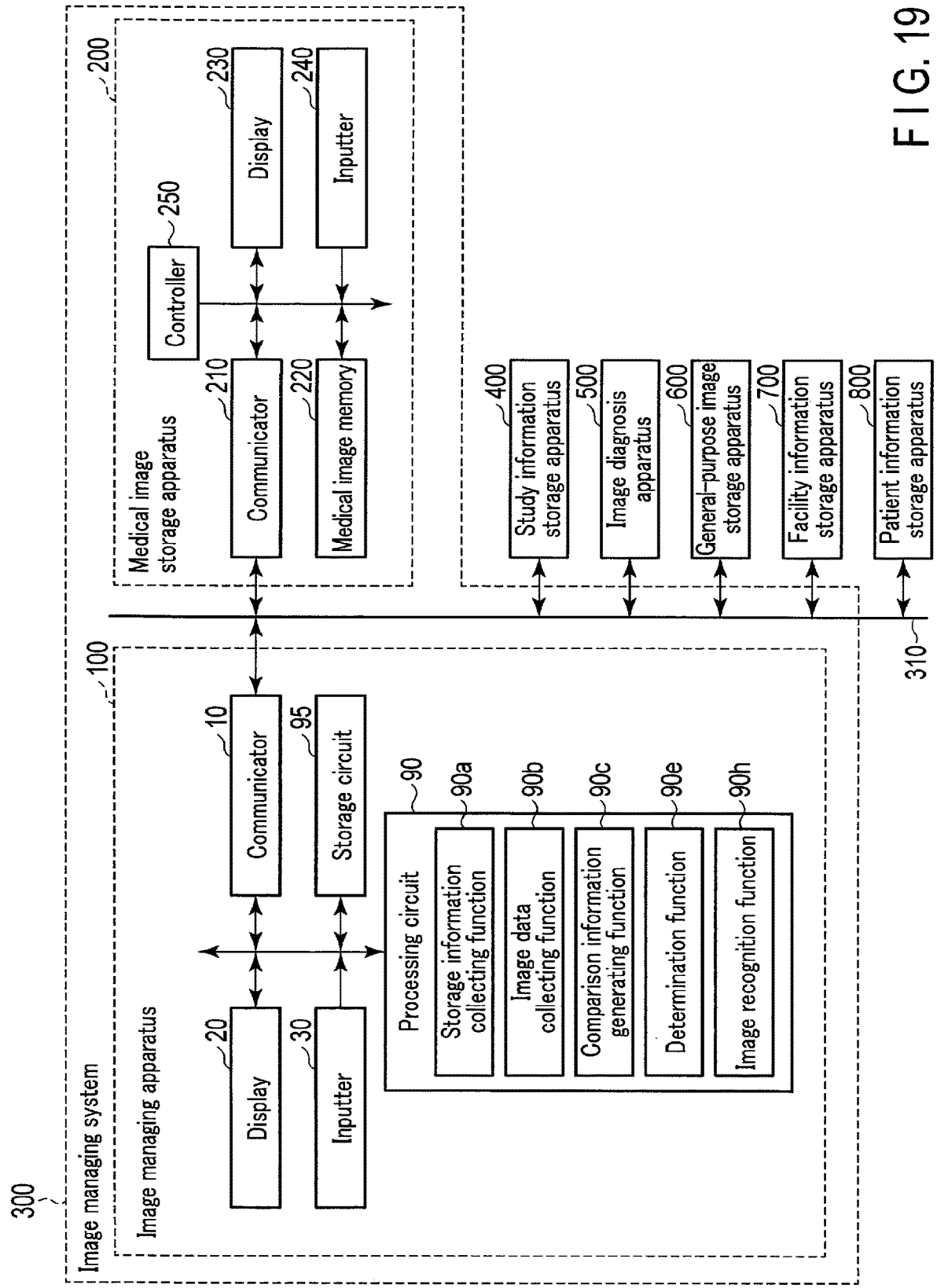
FIG. 19 is a function block diagram showing an example of a medical image processing system according to the fourth embodiment.

FIG. 19 is a function block diagram showing an example of a medical image processing system according to the fourth embodiment. In FIG. 19, elements similar or corresponding to those shown in FIGS. 1 and 17 are denoted by the same reference symbols, and a repetitive description of such elements will be omitted.

After reading the program 95a, the processing circuit 90 has the functions shown in FIG. 19, namely, a storage information collecting function 90a, an image data collecting function 90b, a comparison information generating function 90c, a determination function 90e and an image recognition function 90h. In other words, the processing circuit 90 reads, from the storage circuit 95, programs related to the storage information collecting function 90a, the image data collecting function 90b, the comparison information generating function 90c, the determination function 90e and the image recognition function 90h.

The processing circuit 90 loads the program related to the image recognition function in its memory, and executes the program to realize the image recognition function 90h. At the time, the processing circuit 90 functions as an image recognizer. The image recognition function 90h is a function of collecting symbol information included in the general-purpose image data based on image recognition technology.

The symbol information is specifically character data such as letters and numbers included in the general-purpose image data, and can be extracted using an existing image recognition engine.

The comparison information generating function 90c of the processing circuit 90 is a function of generating comparison information based on the storage information collected by the storage information collecting function 90a, the appendant data collected by the image data collecting function 90b and symbol information collected based on the image data recognition function 90h.

The determination function 90e of the processing circuit 90 is a function of determining whether general-purpose image data is related to the study in which DICOM image data is generated, based on the comparison information generated by the comparison information generating function 90c.

Owing to this feature, comparison information is generated based on the storage information on the general-purpose image data, the appendant data and the symbol information. Therefore, the comparison information includes not only the storage location of the general-purpose image data and the appendant data such as Exif information but also symbol information included in the general-purpose image data. Owing to this, a determination can be made as to whether the general-purpose image data to be associated with the DICOM image data correctly corresponds to the DICOM image data. Accordingly, incorrect image association can be prevented in the fourth embodiment as well.

Fifth Embodiment

Figure 20:
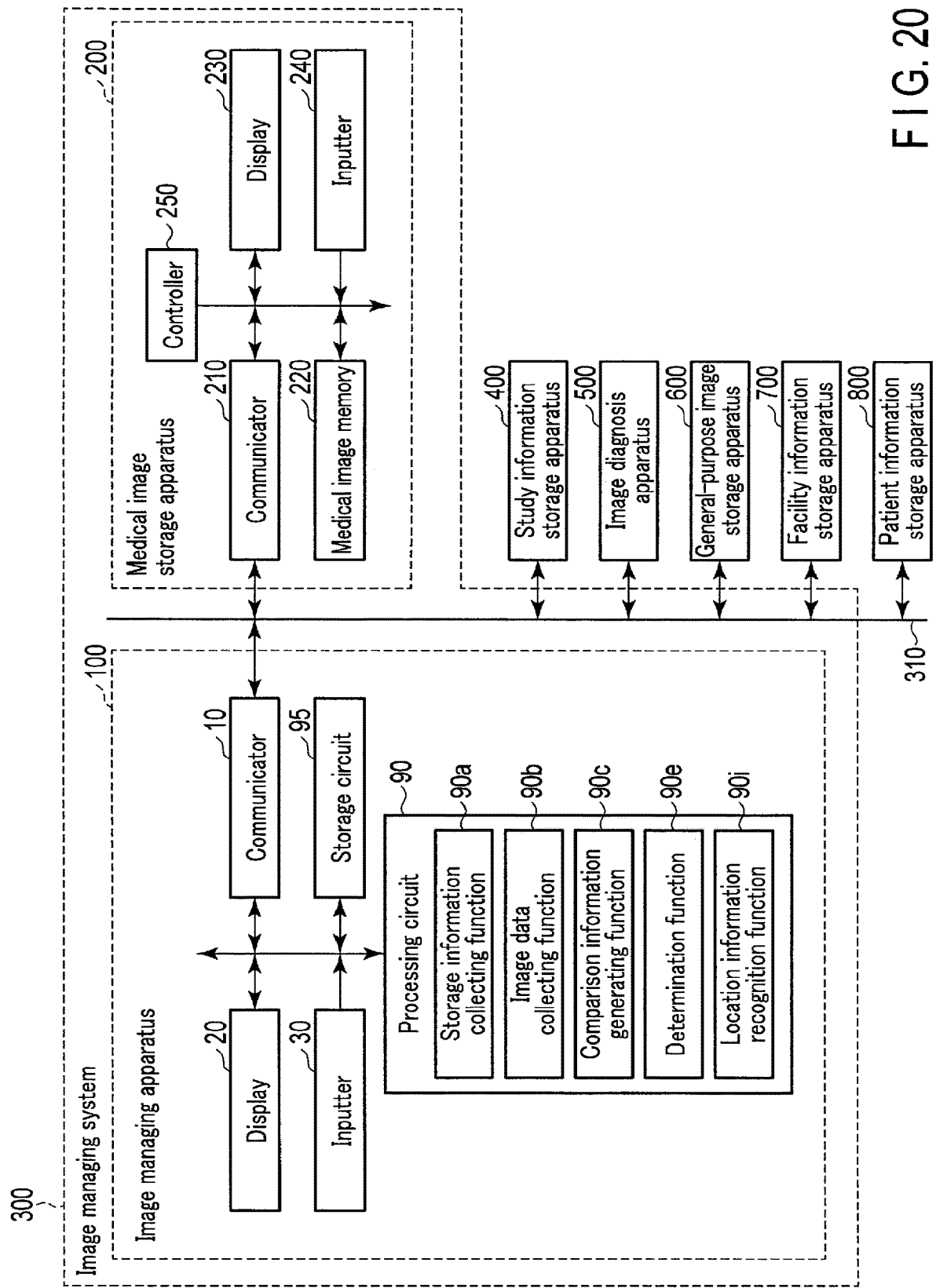
FIG. 20 is a function block diagram showing an example of a medical image processing apparatus according to the fifth embodiment.

FIG. 20 is a function block diagram showing an example of a medical image processing apparatus according to the fifth embodiment. In FIG. 20, elements similar or corresponding to those shown in FIGS. 1 and 17 are denoted by the same reference symbols, and a repetitive description of such elements will be omitted.

After reading the program 95a, the processing circuit 90 has the functions shown in FIG. 20, namely, a storage information collecting function 90a, an image data collecting function 90b, a comparison information generating function 90c, a determination function 90e and a location information recognition function 90i. In other words, the processing circuit 90 reads, from the storage circuit 95, programs related to the storage information collecting function 90a, the image data collecting function 90b, the comparison information generating function 90c, the determination function 90e and the location information recognition function 90i.

The processing circuit 90 loads the program related to the location information recognition function in its memory, and executes the program to realize the location information recognition function 90i. At the time, the processing circuit 90 functions as a location information recognizer. The location information recognition function 90i is a function of recognizing location information representing where the general-purpose image data is generated.

The comparison information generating function 90c of the processing circuit 90 is a function of generating comparison information based on the storage information collected by the storage information collecting function 90a, the appendant data collected by the image data collecting function 90b and location information collected based on the location information recognition function 90i.

The determination function 90e of the processing circuit 90 is a function of determining whether general-purpose image data is related to the study in which DICOM image data is generated, based on the comparison information generated by the comparison information generating function 90c.

Owing to this feature, comparison information is generated based on the storage information on the general-purpose image data, the appendant data and the location information. Therefore, the comparison information that can be obtained includes a combination of the storage location of the general-purpose image data, the appendant data, and the information representing where the apparatus creating the general-purpose image data is located. Owing to this, a determination can be made as to whether the general-purpose image data to be associated with the DICOM image data correctly corresponds to the DICOM image data. Accordingly, incorrect image association can be prevented in the fifth embodiment as well.

Sixth Embodiment

Figure 21:
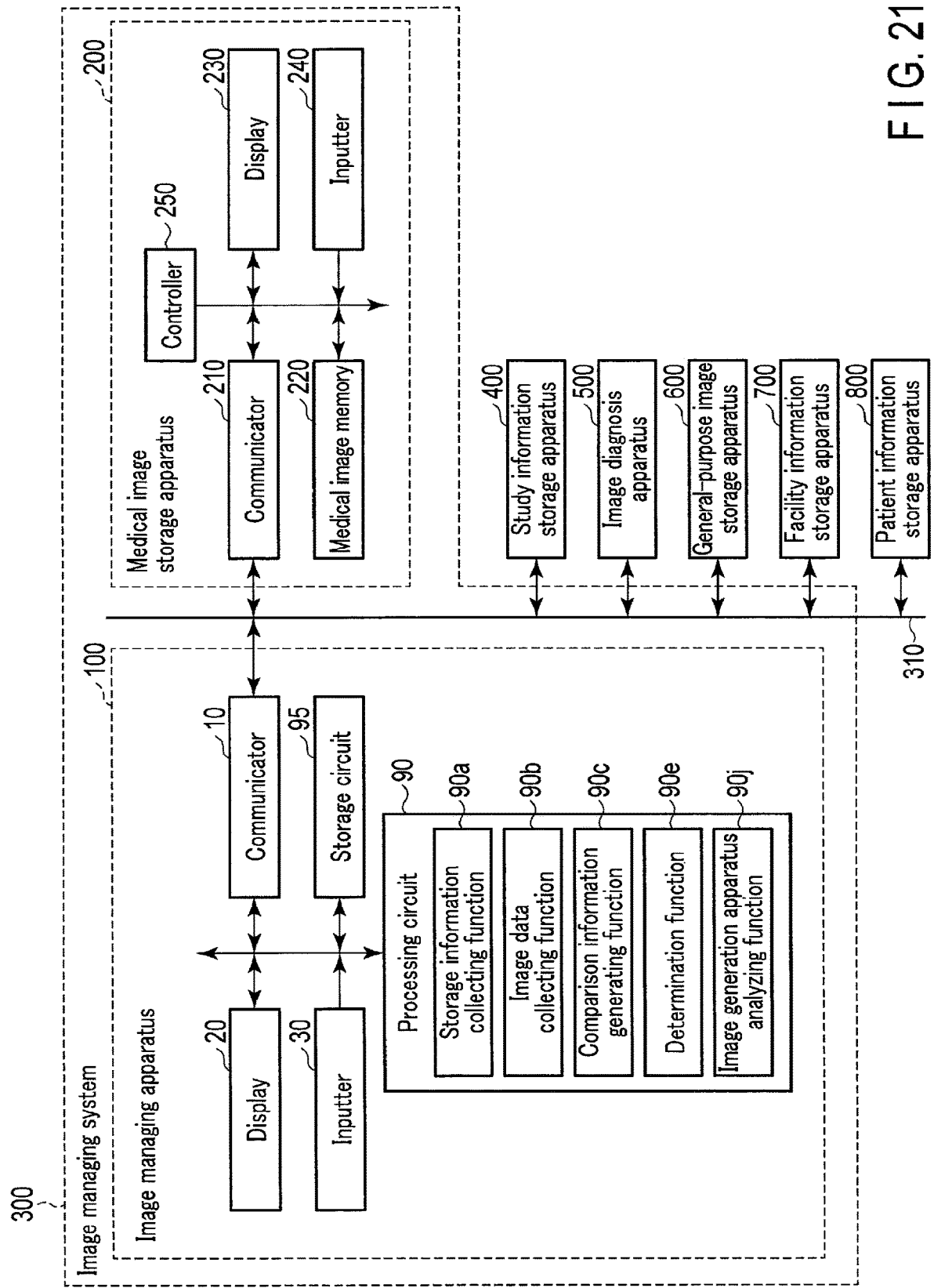
FIG. 21 is a function block diagram showing an example of a medical image processing apparatus according the sixth embodiment.

FIG. 21 is a function block diagram showing an example of a medical image processing apparatus according the sixth embodiment. In FIG. 21, elements similar or corresponding to those shown in FIGS. 1 and 17 are denoted by the same reference symbols, and a repetitive description of such elements will be omitted.

After reading the program 95a, the processing circuit 90 has the functions shown in FIG. 21, namely, a storage information collecting function 90a, an image data collecting function 90b, a comparison information generating function 90c, an image generation apparatus analyzing function 90j. In other words, the processing circuit 90 reads, from the storage circuit 95, programs related to the storage information collecting function 90a, the image data collecting function 90b, the comparison information generating function 90c, the determination function 90e and the image generation apparatus analyzing function 90j.

The processing circuit 90 loads the program related to the image generation apparatus analyzing function in its memory, and executes the program to realize the image generation apparatus analyzing function 90j. At the time, the processing circuit 90 functions as an image generation apparatus analyzer. The image generation apparatus analyzing function 90j is a function of obtaining image generation apparatus information regarding an image generation apparatus that created the general-purpose image data.

The comparison information generating function 90c of the processing circuit 90 is a function of generating comparison information based on the storage information collected by the storage information collecting function 90a, the appendant data collected by the image data collecting function 90b and image generation apparatus information collected by the image generation apparatus analyzing function 90j.

The determination function 90e of the processing circuit 90 is a function of determining whether general-purpose image data is related to the study in which DICOM image data is generated, based on the comparison information generated by the comparison information generating function 90c.

Owing to this feature, comparison information is a combination of the storage information on the general-purpose image data, the appendant data and the identification information on the apparatus that created the general-purpose image data. Therefore, the comparison information that can be obtained includes a combination of not only the storage location of the general-purpose image data and the appendant data but also the identification information on the apparatus creating the general-purpose image data is located. Therefore, a determination can be made as to whether the general-purpose image data to be associated with the DICOM image data correctly corresponds to the DICOM image data. Accordingly, incorrect image association can be prevented in the sixth embodiment as well.

The embodiments described above are not intended as restrictive. For example, in the above-mentioned embodiments, the general-purpose image data and the study information are compared for matching after the "image paste" button is clicked. Instead of this, the designated general-purpose image data and the study information may be compared for matching, immediately after the general-purpose image data to be pasted is designated, i.e., immediately after the "OK" button (FIG. 4) in the window 22 is clicked.

Furthermore, whether or not the general-purpose image data designated by the user is related to the study identified by the study information can be determined by referring to the study information obtained from the study information storage apparatus 400.

In the above-mentioned embodiments, the image managing apparatus 100 obtains files including general-purpose image data from the general-purpose image storage apparatus 600. Instead of this, files including general-purpose image data may be stored in a portable storage device (such as a card memory), and the image managing apparatus 100 may implement a card reader. In this case, the image managing apparatus 100 can obtain files including general-purpose image data from the card reader, not from the storage device in which it is stored. Accordingly, the data portability can be enhanced.

In addition, the file information collector 40, the comparison information generator 70 and the determiner 80 may be provided for the medical image storage apparatus 200. In this case, the medical image storage apparatus 200 may determine whether or not the general-purpose image data designated by the user is related to the study identified by desirable study information.

The programs for realizing the image management system 300 may be recorded in a computer-readable recording medium. In this case, a computer system reads the programs recorded in the recording medium and executes them to realize the image management system 300. The term "computer system" used herein may be an operating system (OS) or may include hardware such as a peripheral device.

The term "processor" used in the above descriptions is, for example, a central processing unit (CPU) or a graphics processing unit (GPU), or may include the following types of circuit: an application-specific integrated circuit (ASIC), a programmable logic device (such as a simple programmable logic device (SPLD), or a complex programmable logic device (CPLD), a field programmable gate array (EPGA) or the like. The processor reads the programs stored in the storage circuit and executes them to realize the respective functions. The programs may be incorporated in the circuit of the processor, instead of storing them in the storage circuit. In this case, the processor reads the programs incorporated in its circuit and executes them to realize the respective functions. The processors described in connection with the above embodiments are not limited to single-circuit processors. A plurality of independent processors may be combined and integrated as one processor having multiple functions. Furthermore, a plurality of structural elements of each of the above embodiments may be integrated as one processor having multiple functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image processing apparatus, comprising:
 a memory to store DICOM (Digital Imaging and Communication in Medicine) image data including study information generated from a study for a patient on a particular date and having a DICOM tag, the DICOM image data being obtained from a medical image diagnosis apparatus; and
 processing circuitry configured to
  collect general-purpose information relating to general-purpose image data incompatible with DICOM, the general-purpose image data not having the DICOM tag and being generated by an apparatus different from the medical image processing apparatus,
  determine whether a date associated with the general-purpose image data is compatible with the particular date of the study which generated the DICOM image data, based on the general-purpose information and the study information,
  output a warning of misidentification of the patient indicating that the patient might be misidentified in response to a result of the determination,
  collect storage information relating to the general-purpose image data,
  generate event information related to the study in which the DICOM image data is generated, and
  collect appendant data pertaining to the general-purpose image data, and/or add, to the general-purpose image data, metadata representing what is indicated by the general-purpose image data,
  generate comparison information based on the storage information, the event information, and at least one of the appendant data and the metadata, and
  determine whether the general-purpose image data is related to the study, based on the generated comparison information.

2. The medical image processing apparatus according to claim 1, wherein the processing circuitry is further configured to determine whether the general-purpose image data is related to the study, based on the general-purpose information, which includes the date and is attached to the general-purpose image data.

3. The medical image processing apparatus according to claim 1, wherein the processing circuitry is further configured to add attribute information representing a kind of study to the general-purpose image data, and
determine whether the general-purpose image data is related to the study, based on the attribute information representing the kind of study.

4. The medical image processing apparatus according to claim 1, wherein the processing circuitry is further configured to determine whether the general-purpose image data is related to the study, based on the general-purpose information of the date attached to the general-purpose image data or date information included in study history records of the patient.

5. The medical image processing apparatus according to claim 2, wherein the processing circuitry is further configured to determine that the general-purpose image data is related to the study when information identical to information other than the date is included in the study information and that the date is within an allowable period determined based on the particular date of the study.

6. The medical image processing apparatus according to claim 1, wherein the processing circuitry is further configured to
generate comparison information based on the general-purpose information, and
determine whether the general-purpose image data is related to the study, based on the comparison information.

7. The medical image processing apparatus according to claim 6, wherein the processing circuitry is further configured to determine that the general-purpose image data is related to the study when study information identical to the generated comparison information is included in information obtained from a study information memory.

8. The medical image processing apparatus according to claim 6, wherein the processing circuitry is further configured to
input metadata representing what is indicated by the general-purpose data, and
collect at least the metadata, information indicating a storage location of the memory in which a file is stored, and information on the date attached to the general-purpose image data,
wherein the comparison information includes information on a kind of study based on the metadata, information on the storage location, and information on the particular date of the study based on the information on the date.

9. The medical image processing apparatus according to claim 1, wherein the processing circuitry is further configured to display the warning.

10. The medical image processing apparatus according to claim 1, wherein the processing circuitry is further configured to
collect the appendant data pertaining to the general-purpose image data;
add, to the general-purpose image data, the metadata representing what is indicated by the general-purpose image data; and
generate the comparison information based on the storage information, the appendant data, the event information, and the metadata.

11. The medical image processing apparatus according to claim 1, wherein the processing circuitry is further configured to
collect storage information relating to the general-purpose image data;
collect appendant data pertaining to the general-purpose image data;
generate comparison information based on the storage information and the appendant data; and
determine whether the general-purpose image data is related to the study, based on the generated comparison information.

12. The medical image processing apparatus according to claim 1, wherein the processing circuitry is further configured to
collect storage information relating to the general-purpose image data;
collect appendant data pertaining to the general-purpose image data;
collect symbol information included in the general-purpose image data based on image recognition technology;
generate comparison information based on the storage information, the appendant data and the symbol information; and
determine whether the general-purpose image data is related to the study, based on the generated comparison information.

13. The medical image processing apparatus according to claim 1, wherein the processing circuitry is further configured to
collect storage information relating to the general-purpose image data;
collect appendant data pertaining to the general-purpose image data;
recognize location information representing where the general-purpose image data is generated;
generate comparison information based on the storage information, the appendant data and the location information; and
determine whether the general-purpose image data is related to the study, based on the generated comparison information.

14. The medical image processing apparatus according to claim 1, wherein the processing circuitry is further configured to
collect storage information relating to the general-purpose image data;
collect appendant data pertaining to the general-purpose image data;
obtain image generation apparatus information regarding an image generation apparatus that created the general-purpose image data; and
generate comparison information based on the storage information, the appendant data and the image generation apparatus information; and
determine whether the general-purpose image data is related to the study, based on the generated comparison information.

15. The medical image processing apparatus of claim 10, wherein the processing circuitry is further configured to collect, as the appendant data, at least one of the data of photography of an image file, a vendor name, position information, and a type of photography device.

* * * * *